United States Patent [19]

Katner

[11] Patent Number: 4,692,443

[45] Date of Patent: Sep. 8, 1987

[54] 3-BICYCLICPYRIDINIUM-METHYL CEPHALOSPORINS

[75] Inventor: Allen S. Katner, Indianapolis, Ind.

[73] Assignee: Eli Lilly and Company, Indianapolis, Ind.

[21] Appl. No.: 679,717

[22] Filed: Dec. 10, 1984

Related U.S. Application Data

[63] Continuation-in-part of Ser. No. 542,619, Oct. 17, 1983, abandoned.

[51] Int. Cl.$^4$ .................. C07D 501/38; A61K 31/545
[52] U.S. Cl. ..................................... 514/206; 514/203; 514/204; 514/205; 540/224; 540/225
[58] Field of Search ................... 544/27, 25; 514/203, 514/204, 206, 205; 540/224, 225

[56] References Cited

U.S. PATENT DOCUMENTS 4,278,793  7/1981  Durckheimer et al. .............. 544/27
4,353,824  10/1982  Schindler et al. .................... 260/156
4,500,526  2/1985  Imae et al. .......................... 514/226

FOREIGN PATENT DOCUMENTS 0097961  1/1984  European Pat. Off. .
2098216  11/1982  United Kingdom .

Primary Examiner—Nicholas S. Rizzo
Attorney, Agent, or Firm—Paul C. Steinhardt; Leroy Whitaker

[57] ABSTRACT

Cephalosporin compounds substituted in the 7-position by a 2-(5- or 6-membered heterocyclic)-2-oximinoacetylamino group and in the 3-position with an imidazolo, oxazolo or thiazolopyridinium-methyl group are broad spectrum antibiotics highly effective in combating bacterial infections of gram-negative and gram-positive microorganisms. The cephalosporins are best prepared by reacting a silylated 7-[2-(heterocyclic)-2-oximinoacetylamino]-3-iodomethyl-3-cephem-4-carboxylic acid with an imidazolopyridine, and oxazolopyridine or a thiazolopyridine. Pharmaceutical formulations comprising a compound of the invention and a method for treating bacterial infections comprising their use are also provided.

59 Claims, No Drawings

3-BICYCLICPYRIDINIUM-METHYL CEPHALOSPORINS

CROSS-REFERENCE

This is a continuation-in-part of Ser. No. 542,619 filed Oct. 17, 1983, now abandoned.

BACKGROUND OF THE INVENTION

This invention relates to cephalosporin antibiotics, to pharmaceutical formulations thereof, and to a method for treating bacterial infections. In particular, it relates to cephalosporin antibiotics which structurally possess a 7-[2-(amino-substituted 5- or 6-membered heterocyclic ring)-2-oximinoacetylamino] side chain and a bicyclic pyridinium-methyl group in the 3-position of the cephalosporin nucleus.

Prior to this invention, a number of cephalosporin antibiotics substituted in the 3-position by a quaternary ammonium methyl and in the 7-position with various acylamino groups were known. Such compounds possess the betaine structure in that the positively-charged nitrogen atom of the quaternary ammonium group exists in the salt form with the anionic form of the $C_4$ carboxy group (carboxylate anion) of the cephalosporin. The well-known cephalosporin antibiotic cephaloridine, 7-(α-thienylacetamido)-3-(pyridinium-1-ylmethyl)-3-cephem-4-carboxylate of the following formula, possesses the betaine structure.

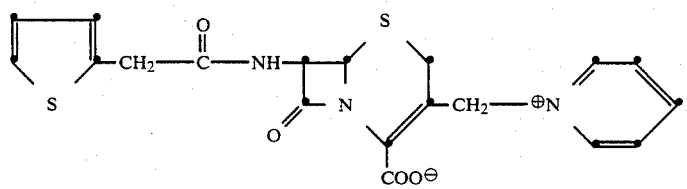

The first cephalosporin of this structural type was discovered by Hale, Newton, and Abraham, *Biochem. J.* 79, 403 (1961), upon the reaction of cephalosporin C with pyridine (cephalosporin $C_A$). Numerous other cephalosporin betaines with differing 7-acylamino side chains have been described since cephalosporin $C_A$ and cephaloridine were discovered.

Recently, Heymes et al., U.S. Pat. No. 4,152,432, described cephalosporin antibiotics having as the 7-acylamino side chain a 7-[2-(2-aminothiazol-4-yl)-2-alkoxyiminoacetylamino] group and as the 3-position substituent an acetoxymethyl group. Others have prepared betaine derivatives of this antibiotic, e.g., as described in U.S. Pat. No. 4,098,888, by Takeda and in U.S. Pat. No. 4,258,041, by O'Callaghan et al.

Because the cephalosporin antibiotics possess potent antibacterial activity, intensive research in efforts to find improved broad spectrum cephalosporin antibiotics continues. In particular, these efforts seek improved cephalosporin antibiotics having potent broad spectrum activity coupled with activity against bacteria and bacterial strains known to be resistant to antibiotics in current use. An object of this invention is to provide a new group of cephalosporins having excellent broad spectrum activity.

SUMMARY OF THE INVENTION

This invention provides semi-synthetic cephalosporin broad spectrum antibiotics defined by the formula 1

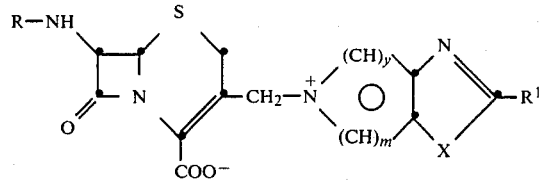

wherein
R is hydrogen, formyl, α-aminoadipoyl, protected α-aminoadipoyl, or an acyl group represented by the formula

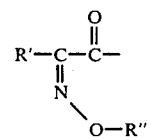

wherein
R' is a 5- or 6-membered heterocyclic ring represented by the formulas

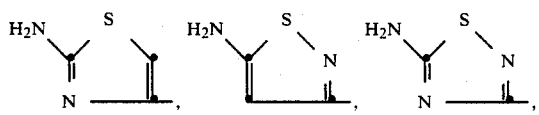

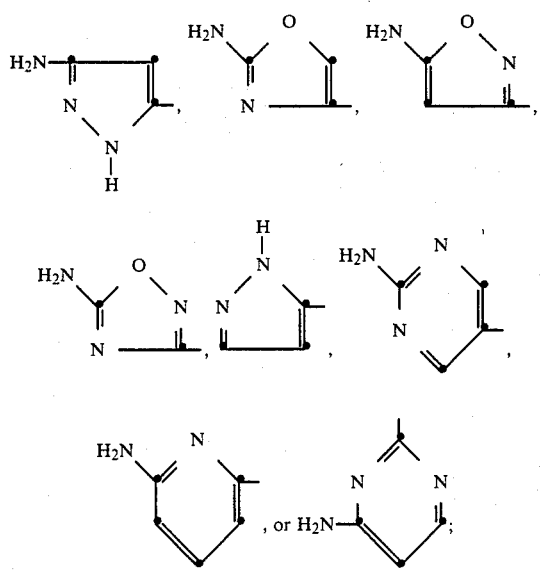

R" is hydrogen, $C_1$–$C_4$ alkyl, a carboxy-substituted alkyl or carboxy-substituted cycloalkyl group represented by the formula

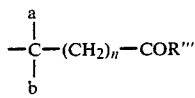

wherein n is 0-3, a and b when taken separately are independently hydrogen or $C_1$-$C_3$ alkyl, or when taken together with the carbon to which they are attached form a $C_3$-$C_7$ carbocyclic ring; R''' is hydroxy, amino, $C_1$-$C_4$ alkoxy, or OR° wherein R° is indanyl, phthalidyl, an acyloxymethyl group of the formula —$CH_2$—OC(O)$R_2$, wherein $R_2$ is $C_1$-$C_4$ alkyl or phenyl; or R° is a carboxy-protecting ester group;

or R'' is an N-substituted carbamoyl group represented by the formula

wherein

R'''' is $C_1$-$C_4$ alkyl, phenyl, or $C_1$-$C_3$ alkyl substituted by phenyl;

y and m independently are integers equal to 0, 1, 2 or 3, provided that y plus m equals 3;

$R^1$ is hydrogen, $C_1$-$C_4$ alkyl, $C_1$-$C_4$ alkoxy, $C_1$-$C_4$ alkylthio, thienyl, amino, $C_1$-$C_4$ alkanoylamino, $C_1$-$C_4$ alkylamino, di-$C_1$-$C_4$ alkylamino, hydroxycarbonyl, $C_1$-$C_4$ alkoxycarbonyl, or phenyl or phenylcarbonyl in which the phenyl groups may be substituted by one or two groups selected from $C_1$-$C_4$ alkoxy, $C_1$-$C_4$ alkyl or $C_1$-$C_4$ alkylthio;

X is O, S or N—$R^2$, where $R^2$ is hydrogen or $C_1$-$C_4$ alkyl; and the pharmaceutically acceptable salts and biologically labile esters thereof.

In a preferred embodiment, R is an acyl group of the formula

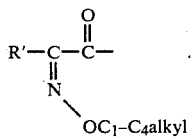

Within this group, R' is preferably

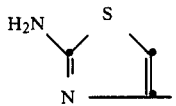

In another preferred embodiment, X in the above formula is N—$R^2$. Also preferred are compounds wherein y is 1 and m is 2.

This invention also provides pharmaceutical formulations comprising a cephalosporin as defined above and a pharmaceutical carrier, excipient or diluent therefor.

Also provided is a method of treating bacterial infections in animals employing a compound of this invention.

DETAILED DESCRIPTION OF THE INVENTION

The terms used in the definition of the compounds of this invention have the following meanings when used herein: "$C_1$-$C_4$ alkyl" refers to methyl, ethyl, n-propyl, isopropyl, n-butyl, t-butyl, sec-butyl, and the like; "$C_1$-$C_4$ alkoxy" refers to methoxy, ethoxy, n-propoxy, isopropoxy, n-butoxy, t-butoxy, sec-butoxy, and the like; "$C_1$-$C_3$ alkyl" refers to methyl, ethyl, n-propyl, and isopropyl; "$C_1$-$C_3$ alkyl substituted by phenyl" refers to benzyl, 2-phenethyl, 1-phenethyl, 3-phenylpropyl, 2-phenylpropyl, and the like; and "$C_3$-$C_7$ carbocyclic ring" refers to cyclopropyl, cyclobutyl, cyclopentyl, cyclohexyl, and cycloheptyl. "$C_1$-$C_4$ Alkanoylamino" refers to formamido, acetamido, propionamido, butyramido, and like acylamino groups. Typical "alkylamino" and "dialkylamino" groups include methylamino, isopropylamino, diethylamino, methyl-n-butylamino, ethyl-sec-butylamino, and the like. Substituted phenyl groups include 2-methoxyphenyl, 3-ethylphenyl, 2-isopropylthiophenyl, 2-methyl-4-ethylthiophenyl, 2-methoxy-4-methylthiophenyl, and the like.

The term "protected α-aminoadipoyl" refers to the α-aminoadipoyl acyl group in which the amino group and the carboxy group are blocked or protected with conventional protecting groups. For example, the amino group can be protected with an acyl or haloacyl group such as acetyl, chloroacetyl, propionyl, benzoyl, chlorobenzoyl, dichloro or dibromobenzoyl, phthaloyl, 2-carboxytetrachlorobenzoyl, 2-carboxytetrabromobenzoyl, and the like; or an alkyloxycarbonyl or aryloxycarbonyl group such as ethoxycarbonyl, trichloroethoxycarbonyl, t-butyloxycarbonyl, t-amyloxycarbonyl, benzyloxycarbonyl, or p-nitrobenzyloxycarbonyl, and like amino protecting groups. Conventional carboxy protecting groups are, for example, the ester forming groups commonly employed in the β-lactam antibiotic art to block or protect the acidic carboxy group during the preparation of antibiotic compounds. Examples of such groups are described hereinafter for the definition of the term R° of the above formula.

The carboxy-substituted alkyl and carboxy-substituted cycloalkyl groups represented by R'' in the above formula when R''' is hydroxy are exemplified by carboxymethyl, 2-carboxyethyl, 3-carboxypropyl, 4-carboxybutyl, 2-carboxyprop-2-yl, 2-carboxyprop-1-yl, 2-methyl-4-carboxybut-2-yl, 3-carboxy-3-methylprop-2-yl, 1-carboxycycloprop-1-yl, 1-carboxycyclobut-1-yl, 1-carboxycyclopent-1-yl, 1-carboxycyclohex-1-yl, 1-carboxymethylcyclobut-1-yl, 2-carboxyethylcyclohex-1-yl, and the like. When in the above formula R''' is $NH_2$, examples of the carboxamides represented are the amides of the above-named carboxy-substituted radicals.

The esters of the carboxy-substituted groups (formula 1, R'' is carboxy-substituted alkyl or cycloalkyl and R''' is $C_1$-$C_4$ alkoxy) are illustrated by methoxycarbonylmethyl, ethoxycarbonylmethyl, 2-(ethoxycarbonyl)-prop-2-yl, 1-propoxycarbonylcyclopent-1-yl, and like $C_1$-$C_4$ alkyl esters of the above-named carboxy-substituted alkyl and cycloalkyl radicals.

Examples of N-substituted carbamoyl groups (eg. formula 1, R'' is carbamoyl) are N-methylcarbamoyl, N-ethylcarbamoyl, N-propylcarbamoyl, N-phenylcarbamoyl, N-benzylcarbamoyl, and the like.

The compounds of this invention are characterized in part by the bicyclic pyridinium group attached to the 3-methyl group of the cephalosporin nucleus. Typical bicyclic pyridines that can be employed in the synthesis of the pyridinium-methyl derivatives of this invention are illustrated below. The numbering system to be employed in naming invention compounds is indicated in the following formulas.

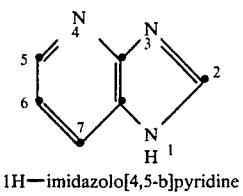
1H—imidazolo[4,5-b]pyridine

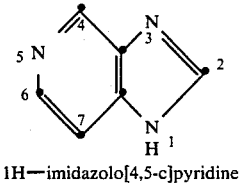
1H—imidazolo[4,5-c]pyridine

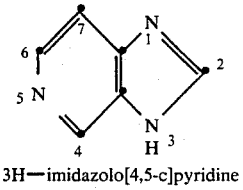
3H—imidazolo[4,5-c]pyridine

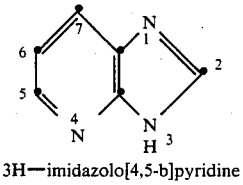
3H—imidazolo[4,5-b]pyridine

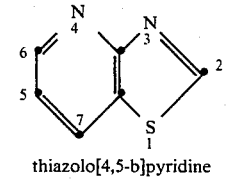
thiazolo[4,5-b]pyridine

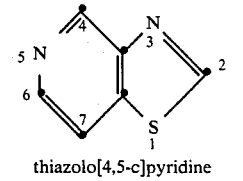
thiazolo[4,5-c]pyridine

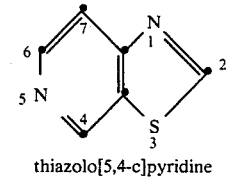
thiazolo[5,4-c]pyridine

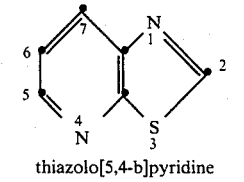
thiazolo[5,4-b]pyridine

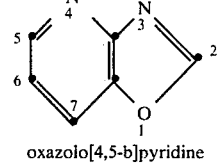
oxazolo[4,5-b]pyridine

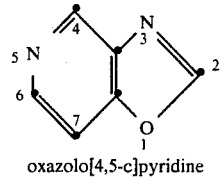
oxazolo[4,5-c]pyridine

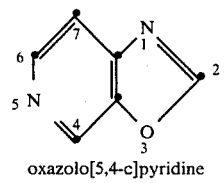
oxazolo[5,4-c]pyridine

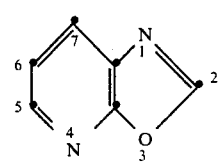
oxazolo[5,4-b]pyridine

The imidazolopyridines, oxazolopyridines and thiazolopyridines that are required starting materials are known compounds and are synthesized employing art known procedures. See for example, J. Heterocyclic Chem., 14, 1045 (1977), Chemical Abstracts, 50, 335h and 50, 1000i. Typical bicyclicpyridines to be employed in preparing compounds of this invention include the following:

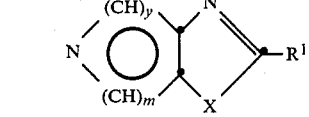

| y | m | X | $R^1$ |
|---|---|---|---|
| 1 | 2 | S | 2-methyl-3-ethoxyphenyl |
| 1 | 2 | S | $OCH_3$ |
| 1 | 2 | S | $SCH_2CH_3$ |
| 2 | 1 | O | $SCH_2CH(CH_3)_2$ |
| 0 | 3 | S | $CH(CH_3)_2$ |
| 2 | 1 | N | COOH |
| 3 | 0 | N | $N(CH_3)_2$ |
| 1 | 2 | S | $NH_2$ |
| 1 | 2 | S | $NHCH_2CH_3$ |
| 2 | 1 | O | phenyl |
| 2 | 1 | N | 2-methylphenyl |
| 2 | 1 | S | 2-methyl-3-ethoxyphenyl |
| 3 | 0 | S | $N\begin{matrix}CH_3\\CH_2CH_3\end{matrix}$ |
| 1 | 2 | O | $COOCH_3$ |
| 2 | 1 | S | benzoyl |
| 2 | 1 | N | 3-thienyl |
| 2 | 1 | S | H |

-continued

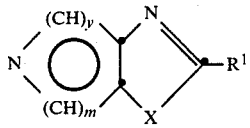

| y | m | X | R¹ |
|---|---|---|---|
| 1 | 2 | S | 3-methylthiobenzoyl |

Especially preferred compounds of the invention are those prepared with thiazolopyridines, for instance compounds of the formulas

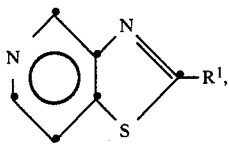

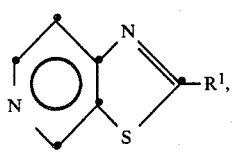

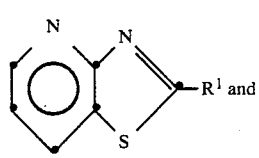

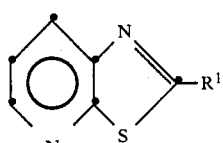

wherein $R^1$ is as defined above. The most preferred compounds of the invention have the formula

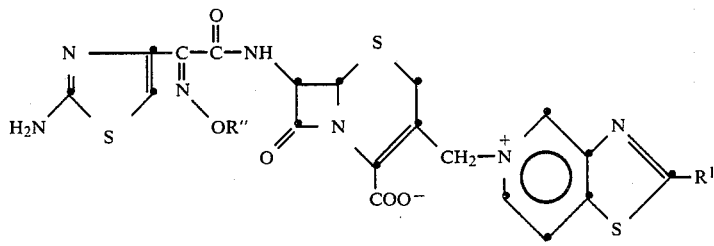

where $R''$ and $R^1$ are as defined above, but wherein $R''$ and $R^1$ both are most preferably $C_1$-$C_4$ alkyl such as methyl or the like.

Carboxy-protected derivatives of the compounds represented by the above formula 1 when $R''$ is a carboxy-substituted alkyl or carboxy-substituted cycloalkyl group and $R'''$ is $OR°$, are esters of the carboxy group commonly known in the art as carboxy-protecting or blocking groups. Examples of such ester groups ($R°$) are alkyl, alkenyl, and substituted alkyl ester groups such as t-butyl, 2-methylbutene-2-yl, 2,2,2-trichloroethyl, 2,2,2-tribromoethyl, and 2-iodoethyl; the benzyl ester and substituted benzyl esters such as p-methoxybenzyl and p-nitrobenzyl; the diphenylmethyl ester and substituted diphenylmethyl esters such as the 4-methoxydiphenylmethyl and 4,4'-dimethoxydiphenylmethyl esters; and trialkylsilyl esters such as trimethylsilyl; and like ester groups. The carboxy-protecting group is used for the temporary protection of the carboxy group as, for example, during the preparation of the compounds. These groups are readily removed under hydrolysis or hydrogenolytic conditions which are generally known in the art.

The esters defined by the above formula 1 when $R''$ is a carboxy-substituted alkyl or a carboxy-substituted cycloalkyl group and $R'''$ is $OR°$, namely the indanyl, phthalidyl, and acyloxymethyl esters, are biologically cleavable esters. Examples of such esters are the 5-indanyl, phthalidyl, acetoxymethyl, propionoxymethyl, pivaloyloxymethyl, and benzoyloxymethyl esters. The biologically cleavable esters are obtained by reacting the carboxylic acid function in the salt form, eg. the sodium or potassium salt, with bromophthalide, or with an acyloxymethyl halide, eg. acetoxymethyl bromide or pivaloyloxymethyl bromide. The indanyl ester is prepared with 5-indanol, the cephalosporin acid and a condensing agent such as DCC or EEDQ.

The heterocyclic rings represented by $R'$ in the above formula 1 are named herein as follows: 2-aminothiazol-4-yl, 5-aminoisothiazol-3-yl, 5-amino-1,2,4-thiadiazol-3-yl, pyrazol-5-yl, 3-aminopyrazol-5-yl, 2-aminopyrimidin-5-yl, 4-aminopyrimidin-2-yl, 2-aminopyridin-6-yl, 2-aminooxazol-4-yl, 5-aminoisoxazol-3-yl, and 5-amino-1,2,4-oxadiazol-3-yl.

In the description of the compounds of the invention, the term "oximino" is used for convenience in describing the oxime and substituted oxime function

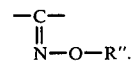

The compounds of the invention wherein R is an acyl group of the formula

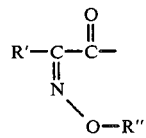

are broad spectrum antibiotics which inhibit the growth of microorganisms pathogenic to man and animals. For example, these compounds are effective in controlling the growth of the staphylococci and streptococci and penicillin-resistant strains of staphylococci. They also inhibit the growth of the gram-negative bacteria, for example proteus, pseudomonas, enterobacter, *Escherichia coli*, Klebsiella, Shigella, Serratia, and Salmonella.

The compounds represented by the above formula wherein R is hydrogen, formyl, aminoadipoyl, or protected aminoadipoyl are intermediates useful in the preparation of the compounds wherein R is an acyl group as described hereinafter.

The compounds of the invention wherein R is an acyl group as defined above are prepared by the reaction of a bicyclicpyridine(imidazolopyridine, oxazolopyridine or thiazolopyridine) with a 7-acylaminocephalosporin represented by the formula 2

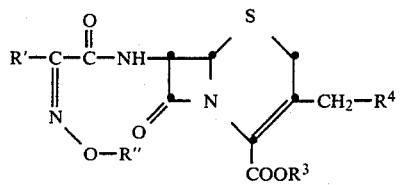

wherein R' and R" have the same meanings as defined hereinabove, $R^3$ is hydrogen or a carboxy-protecting group, and $R^4$ is chloro, bromo, iodo, or acetoxy. The displacement reaction is preferably carried out with a compound of the formula 2 wherein $R^4$ is acetoxy or iodo.

In a preferred method, a compound of the above formula wherein $R^4$ is iodo is first prepared by the reaction of a compound wherein $R^4$ is acetoxy and $R^3$ is an ester group with trimethylsilyliodide (trimethyliodosilane, TMSI) by the method of Bonjouklian, U.S. Pat. No. 4,266,049 issued May 5, 1981. The 3-iodomethyl cephalosporin is then reacted with the bicyclicpyridine to provide a compound of the invention.

In carrying out the process, a compound of the above formula wherein $R^4$ is acetoxy is first silylated to form the silyl ester of the $C_4$ carboxy group and with other silyl reactive groups. The silylation is carried out at room temperature in an aprotic organic solvent with a silylating reagent such as mono- or bis-trimethylsilylacetamide, mono-trimethylsilyltrifluoroacetamide, or N-methyl-N-trimethylsilyltrifluoroacetamide. The silylated derivative is then reacted at ambient temperature with trimethylsilyliodide to provide the silylated 3-iodomethyl cephalosporin. The silylated 3-iodomethyl cephalosporin is then reacted with the bicyclicpyridine to provide a silylated compound of the invention. Hydrolysis of the silyl groups provides a compound of the invention.

The process is illustrated by the following reaction scheme wherein a trimethyl silylating reagent and a 1H-imidazolo[4,5-c]pyridine are exemplified.

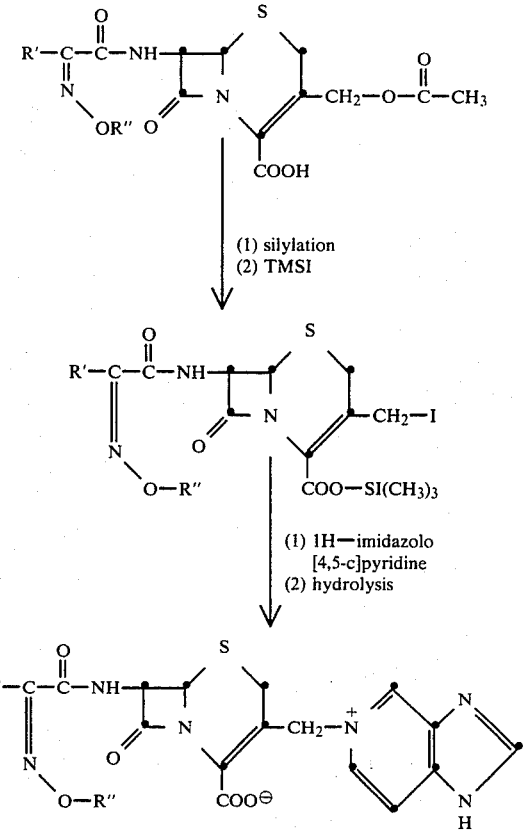

In the above scheme, R' and R" have the same meanings as defined hereinabove.

Alternatively, the antibiotic compounds of the invention are prepared directly from a 3-acetoxymethyl cephalosporin compound (eg. $R^4$ is acetoxy, $R^3$ is H) by displacement of the acetoxy group with the bicyclicpyridine. The preparation is carried out in a known manner, for instance, in an aqueous medium, for example in a water miscible organic solvent containing water. The addition of a small amount of an alkali metal iodide such as potassium iodide can enhance the rate of the reaction. The reaction is carried out at a temperature between about 35° C. and about 70° C. Water miscible organic solvents such as acetone, acetonitrile, tetrahydrofuran, and dimethylacetamide are useful solvents.

This invention also provides the compounds represented by the above formula 1 in the form of salts formed with strong acids and the salt form of biologically labile esters. Such salts are represented by the following formula 3

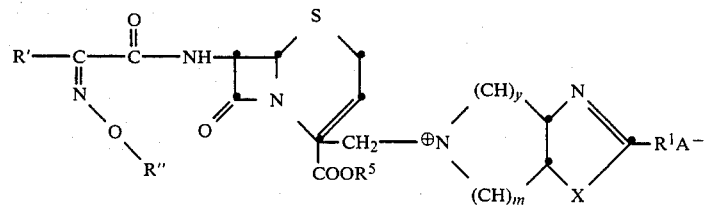

wherein R', R", and $R^1$ have the same meanings as defined above and $R^5$ is hydrogen, indanyl, phthalidyl, or an acyloxymethyl group represented by the formula

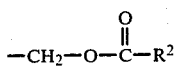

wherein R² has the same meanings as defined hereinabove; and A⁻ is an anion such as chloride, bromide, iodide, sulfate, or phosphate.

Examples of acyloxymethyl ester groups, R⁵, are acetoxymethyl, propionoxymethyl, pivaloyloxymethyl, and benzoyloxymethyl groups.

A compound of the formula 1 is converted to its strong acid salt by reaction with about one molar equivalent or excess of an acid such as hydrochloric acid, hydrobromic acid, sulfuric acid, or phosphoric acid.

The biologically labile esters are prepared with a compound of the formula 1 and an acyloxymethyl halide, an indanyl halide eg. 5-bromoindane or phthalidyl bromide. Upon esterification the salt form of the ester is obtained. For example, with acetoxymethyl bromide the acetoxymethyl ester bromide is obtained (formula 3, R² is acetoxymethyl, A⁻ is Br⁻).

It will be appreciated that when in a compound represented by the formula 1 R″ is a carboxy-substituted alkyl or cycloalkyl group and R‴ is hydroxy, the dibiologically labile esters may be prepared. Likewise it will be appreciated that acid addition salts will be formed with any basic amino groups present in the molecule (i.e. formula 1 wherein an amino-substituted heterocyclic group is present) when the strong acid salts represented by formula 3 are prepared.

The biologically labile ester salts and the strong acid salts represented by the formula 3 are alternative forms of the compounds represented by the formula 1 and may be formulated for administration in therapy.

The compounds of the formula 1, wherein R is hydrogen or formyl, are prepared with 7-aminocephalosporanic acid and 7-formamidocephalosporanic acid, respectively, by displacement of the 3′-acetoxy group with the bicyclicpyridine as described above. Alternatively, 7-formamido-3-iodomethyl-3-cephem-4-carboxylic acid trimethylsilyl ester is prepared by the Bonjouklian method as described above and is then reacted with the bicyclicpyridine to provide the compound of the formula 1 wherein R is formyl.

Alternatively, the 7-amino nucleus compounds of the formula 1 (R is H) are prepared by the well-known N-deacylation reaction which proceeds through an imino chloride to an imino ether and thence on decomposition of the latter to the 7-amino-3-bicyclicpyridinium-4-carboxylate. Initially, 7-acylaminocephalosporanic acid, wherein the 7-acyl group can be for example phenylacetyl, phenoxyacetyl or a heterocyclic acyl group such as thienylacetyl, is reacted with the bicyclicpyridine to form the 7-acylamino-3-bicyclicpyridiniummethyl)-3-cephem-4-carboxylate. Alternatively, the latter compound is obtained via the 7-acylamino-3-iodomethyl ester (Bonjouklian method) which is allowed to react with the bicyclicpyridine. The 7-acyl bicyclopyridinium compound is then treated with an imino halide-forming reagent such as phosphorus pentachloride in an inert solvent in the presence of an acid-binding agent such as a tertiary amine e.g., diethylaniline to provide the imino halide derivative of the 7-position acylamido group. Without isolation, the imino halide is treated with an alcohol, alkanediol or benzyl alcohol to form the corresponding imino ether. Decomposition of the imino ether, for example by aqueous hydrolysis, provides the 7-amino nucleus compound.

In an example of the preparation of a 7-amino nucleus compound by this method, 7-(2-thienylacetamido)cephalosporanic acid is reacted with 1H-imidazolo[4,5-b]pyridine to prepare 7-(2-thienylacetamido)-3-(1H-imidazolo[4,5-b]pyridinium-4-ylmethyl)-3-cephem-4-carboxylate. The latter is converted to the trimethylsilyl ester with trimethylchlorosilane in a halogenated hydrocarbon solvent in the presence of a weak base such as dimethylacetamide in an amount corresponding to a 4-5 molar excess. Solvents such as methylene chloride, trichloroethane, and chloroform are suitable. The solution of the silyl ester is cooled to a temperature of about −30° C. to about 0° C. and an imino halide-forming reagent such as phosphorus pentachloride is added. After imino halide formation is complete, a C₁-C₄ alkanol, an alkanediol, or a benzyl alcohol is added to the cold reaction mixture. The temperature of the reaction mixture is allowed to warm to about room temperature and the product, 7-amino-3-(1H-imidazolo[4,5-b]pyridinium-4-ylmethyl)-3-cephem-4-carboxylic acid, precipitates in the form of the dihydrochloride salt represented by the formula

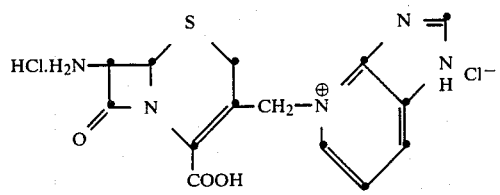

The invention provides the cephalosporin nucleus compounds of the formula

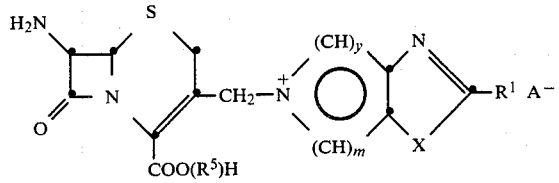

wherein R¹, y, m, A⁻ and R⁵ are as defined above.

The N-formyl compounds (formula 1, R is formyl) are useful as intermediates in the preparation of the antibiotic compounds of the invention. For example, 7-formamidocephalosporanic acid is silylated and the silyl ester converted to the 3-iodomethyl derivative with trimethylsilyliodide as described hereinabove. The 3-iodomethyl silylated derivative is reacted with the bicyclicpyridine to form the compound represented by the formula 1. The N-formyl-3-bicyclicpyridiniummethyl-3-cephem is then converted to the 7-amino nucleus compound with methanolic hydrochloric acid.

The 7-amino-3-(bicyclicpyridinium-methyl)-3-cephem-4-carboxylate or the dihydrochloride salt thereof is also obtained with cephalosporin C wherein the amino and carboxy groups are protected. For example, cephalosporin C is first silylated with a conventional silylating reagent such as N-methyl-N-trimethylsilyltrifluoroacetamide to form the N-trimethylsilyl di-trimethylsilyl ester derivative. The latter is reacted with TMSI by the Bonjouklian method, and the 3-iodomethyl silylated derivative of cephalosporin C which is obtained is then allowed to react with the bicyclicpyridine and, following hydrolysis of the silyl groups, the compound of the formula 1 wherein R is α-aminoadipoyl is obtained. The α-aminoadipoyl side chain is cleaved by the N-deacylation procedure described above. In carrying out the N-deacylation, the amino group and the carboxy groups of the molecule are protected.

In carrying out the preparation of a 7-amino-3-(bicyclicpyridinium-methyl)-3-cephem-4-carboxylate with cephalosporin C, use can be made of the silylated 3-(bicyclicpyridinium-methyl) derivative obtained in the Bonjouklian method as described above. Since the amino group and the two carboxy groups are silylated, and thus protected, the N-deacylation can be carried out directly on this protected intermediate. During the final step of the N-deacylation, i.e. following the formation of the imino ether of the side chain moiety, water is added to effect the hydrolysis of the silyl protecting group. The above-described preparation is illustrated by the following reaction scheme.

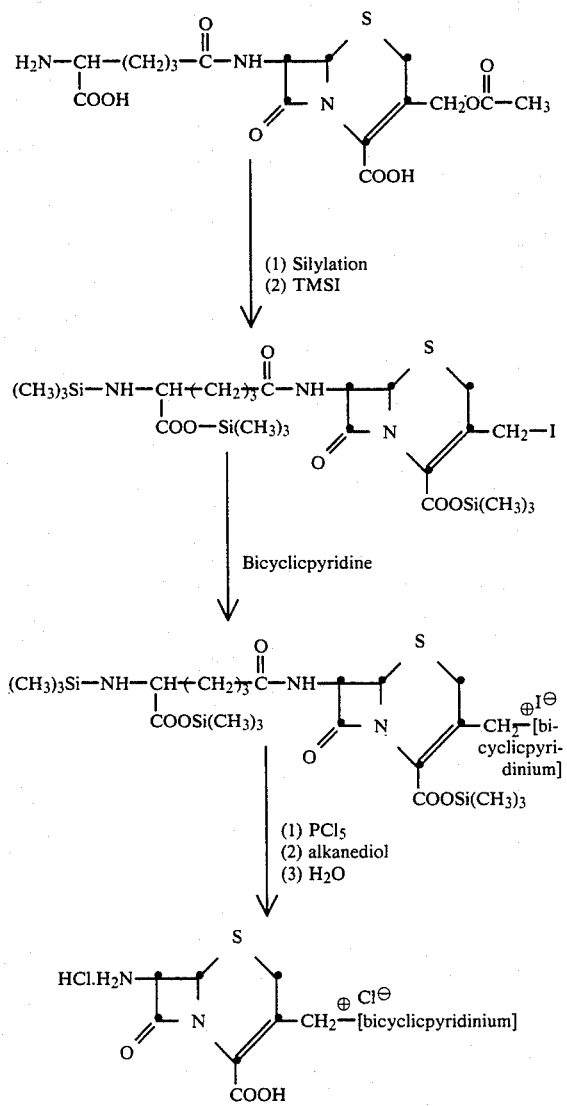

Alternatively, the 7-amino-3-(bicyclicpyridinium-methyl) nucleus compound can be obtained with cephalosporin C having the amino group and the carboxy groups protected. Examples of such protecting groups which can be used are given hereinabove for the definition of the term "protected aminoadipoyl".

The 7-amino nucleus compound (formula 1, R=H) prepared by the N-deacylation method or via the N-formyl derivative is acylated with an active carboxy derivative of a 2-(heterocyclic)-2-oximinoacetic acid represented by the formula

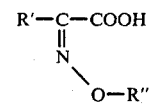

to provide an antibiotic compound of the formula 1. The N-acylation coupling reaction is carried out by acylation methods well-known in the art. Active derivatives of the carboxy group such as the so-called "active esters" can be used. Examples of active esters are those formed with the oximino acetic acid and hydroxybenzotriazole (HBT), or hydroxysuccinimide; and the esters formed with methyl chloroformate and isobutyl chloroformate. The acylation can also be carried out by employing the acid halide, e.g. the acid chloride, in the presence of an acid scavenger such as sodium bicarbonate or triethylamine.

The amino group of the amino-substituted heterocycles (R' in formula 1) is desirably protected during the N-acylation of the 7-amino nucleus compound. Amino-protecting groups which can be used are those commonly employed in the cephalosporin art for the temporary protection of basic amino groups to block or prevent their interference in a reaction carried out at another site in the molecule. Examples of such groups are the haloacyl groups such as chloroacetyl and dichloroacetyl; the urethane-forming protecting groups such as t-butyloxycarbonyl, 2,2,2-trichloroethoxycarbonyl, cyclopentyloxycarbonyl, adamantyloxycarbonyl, benzyloxycarbonyl, p-nitrobenzyloxycarbonyl, and diphenylmethyloxycarbonyl; and other protecting groups such as trityl (triphenylmethyl) and benzhydryl.

The compounds represented by the formula 2 wherein $R^4$ is an acetoxy group are prepared by known methods. For example, compounds wherein R' is the 2-aminothiazol-4-yl group are described by Heymes et al., U.S. Pat. No. 4,152,432; compounds wherein R' is 2-aminopyridin-6-yl, 2-aminopyrimidin-5-yl, or 4-aminopyrimidin-2-yl, are described by U.S. Pat. No. 4,167,176; compounds wherein R' is 5-amino-1,2,4-thiadiazol-3-yl are described by EPO Application No. 0,007,470; compounds wherein R' is 2-aminooxazol-4-yl, 5-amino-1,2,4-oxadiazol-3-yl or 5-aminoisoxazol-3-yl are described in U.S. Pat. No. 4,406,898; compounds wherein R" is an N-substituted carbamoyl group are prepared by the methods described by U.S. Pat. No. 4,200,575; and compounds wherein R' is 3-aminopyrazol-5-yl, or pyrazol-5-yl are obtained as described by U.K. Patent Application No. 2,046,734A.

Commonly, the compounds of the formula 2 wherein $R^4$ is acetoxy are prepared by the N-acylation of the 7-amino group of 7-aminocephalosporanic acid, or an ester thereof, with the 2-(heterocyclic)-2-oximinoacetic acid by employing acylation methods known in the art. For example, the heterocyclic oximino-substituted acetic acid is converted to an active ester such as the ester formed with hydroxybenzotriazole or hydroxysuccinimide, and the active ester is used as the acylating moiety. Other active derivatives of the carboxylic acid such as the acid chloride or acid azide can be used in the acylation.

The compounds of the formula 2 wherein R' is a pyrazol-5-yl or 3-aminopyrazol-5-yl group are prepared by employing methods known in the art. The 2-(pyrazol-5-yl)-2-oximinoacetic acid or the 2-(3-aminopyrazol-5-yl)-2-oximinoacetic acid is prepared and converted to an active derivative of the carboxylic acid, for example, an active ester. The active ester is coupled, via N-acylation, with 7-aminocephalosporanic acid and the 7-[2-(pyrazol-5-yl)-2-oximinoacetamido]-3-acetoxymethyl-3-cephem-4-carboxylic acid and 7-[2-(3-aminopyrazol-5-yl)-2-oximinoacetamido]-3-acetoxymethyl-3-cephem-4-carboxylic acid are converted to the corresponding 3-iodomethyl silylated derivatives as described herein. The latter are reacted with the thienopyridine to provide the respective compound of the invention.

The pyrazole and aminopyrazole oximino substituted acetic acids are prepared by employing synthetic methods known in the art. For example, the 2-(pyrazol-5-yl)-2-alkoxyiminoacetic acid is prepared by heating in an inert hydrocarbon solvent the acetyl oximino compound of the formula A

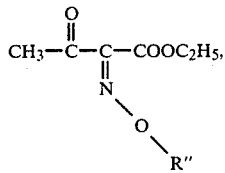

wherein R" is other than hydrogen as defined above, with dimethylformamide dimethylacetal to form the dimethylaminomethylene oximino ester of the formula

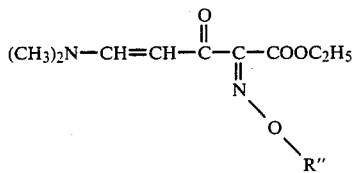

The latter is reacted with hydrazine hydrate to provide the ethyl ester of 2-(pyrazol-5-yl)-2-alkoxyiminoacetic acid. The ester is hydrolyzed to the free acid and the acid converted to an active ester for acylation.

The 2-(3-aminopyrazol-5-yl)-2-alkoxyiminoacetic acid is prepared by reacting the compound of the formula A with carbon disulfide and two equivalents of methyl iodide to form the intermediate compound of the formula B

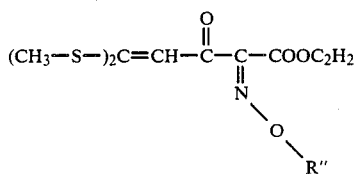

Intermediate B is reacted with N-t-BOC hydrazine to provide compound C,

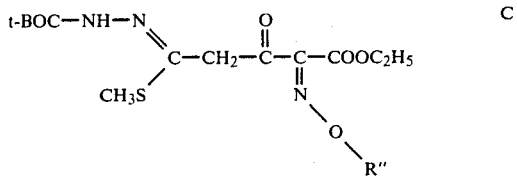

and C is reacted with hydrazine hydrate to form 2-(3-t-BOC-hydrazinopyrazol-5-yl)-2-oximinoacetic acid ethyl ester D.

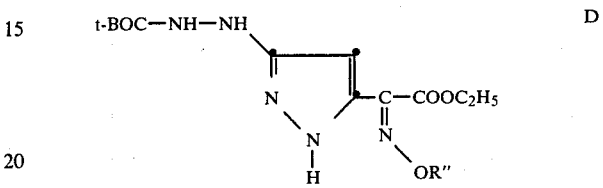

Compound D is treated in the cold with trifluoroacetic acid to remove the t-BOC group and the 3-hydrazinopyrazole is nitrosated with nitrous ($HNO_2$) acid in the cold to form 2-(3-azidopyrazol-5-yl)-2-oximinoacetic acid ethyl ester. The azido group is reduced to the amino group by chemical reduction to provide the 2-(3-aminopyrazol-5-yl)-oximinoacetic acid ethyl ester. The ester is hydrolyzed under alkaline conditions to the free acid.

The compounds of the invention have the same stereochemistry as the known cephalosporin antibiotics. The 7-position side chain has the natural $\beta$-configuration (6R, 7R), while the oximino group in the side chain can exist in either the syn or anti forms or as a mixture of both. Compounds of the invention in either form are prepared by employing the 2-(heterocyclic)-2-oximinoacetic acid acylating moiety in the syn or anti form. Alternatively, mixtures of the syn and anti compounds of the formula 1 can be separated by chromatographic means such as by HPLC. The compounds in the syn form are preferred because of their higher activity.

Examples of bicyclicpyridinium compounds of the invention represented by the formula 1 wherein R is an acyl group include the following compounds:

7-[2-(2-aminothiazol-4-yl)-2-hydroxyiminoacetamido]-3-(1H-imidazolo[4,5-b]pyridinium-4-ylmethyl)-3-cephem-4-carboxylate, 7-[2-(2-aminothiazol-4-yl)-2-methoxyiminoacetamido]-3-(1H-imidazolo[4,5-c]pyridinium-5-ylmethyl)-3-cephem-4-carboxylate, 7-[2-(2-aminothiazole-4-yl)-2-ethoxycarbonylmethoxyiminoacetamido]-3-(3H-imidazolo[4,5-c]pyridinium-5-ylmethyl)-3-cephem-4-carboxylate, 7-[2-(2-aminothiazole-4-yl)-2-methoxyiminoacetamido]-3-(3H-imidazolo[4,5-b]pyridinium-4-ylmethyl)-3-cephem-4-carboxylate, 7-[2-(2-aminothiazol-4-yl)-2-methoxyiminoacetamido]-3-(thiazolo[4,5-c]pyridinium-5-ylmethyl)-3-cephem-4-carboxylate, 7-[2-(2-aminothiazol-4-yl)-2-methoxyiminoacetamido]-3-(thiazole[4,5-b]pyridinium-4-ylmethyl)-3-cephem-4-carboxylate, 7-[2-(2-aminothiazol-4-yl)-2-methoxyiminoacetamido]-3-(thiazolo[5,4-c]pyridinium-5-ylmethyl)-3-cephem-4-carboxylate, 7-[2-(2-aminothiazol-4-yl)-2-methoxyiminoacetamido]-3-(thiazolo[5,4-b]pyridinium-4-ylmethyl)-3-cephem-4-carboxylate, 7-[2-(2-aminopyridin-6-yl)-2-(2-carboxypropyl)xyiminoacetamido]-3-(oxazolo[4,5-b]pyridinium-4-ylmethyl)-3-cephem-4-carboxylate, 7-[2-(5-amino-1,2,4-thiadiazol-3-yl)-2-methoxyiminoacetamido]-3-(oxazolo[4,5-c]pyridinium-5-ylmethyl)-3-cephem-4-carboxylate, 7-[2-(5-aminoisothiazol-3-yl)-2-(2-carboxyprop-2-yl)oxyiminoacetamido]-3-(oxazolo[5,4-c]pyridinium-5-ylmethyl)-3-cephem-4-carboxylate, 7-[2-(2-aminopyrimidin-5-yl)-2-ethoxyiminoacetamido]-3-(oxazolo[5,4-b]pyridinium-4-ylmethyl)-3-cephem-4-carboxylate, 7-[2-(4-aminopyrimidin-2-yl)-2-(N-methylcarbamoyloxy)iminoacetamido]-3-(1H-2-methylimidazolo[4,5-b]pyridinium-4-ylmethyl)-3-cephem-4-carboxylate, 7-[2-(2-aminopyridin-6-yl)-2-methoxyiminoacetamido]-3-(3H-2-phenylimidazolo[4,5-b]pyridinium-4-ylmethyl)-3-cephem-4-carboxylate, 7-[2-(3-aminopyrazol-5-yl)-2-methoxyiminoacetamido]-3-(2-ethylthiazolo[5,4-c]pyridinium-5-ylmethyl)-3-cephem-4-carboxylate, 7-[2-(2-aminoöxazol-4-yl)-2-ethoxycarbonylmethoxyiminoacetamido]-3-(2-aminoöxazolo[5,4-c]pyridinium-5-ylmethyl)-3-cephem-4-carboxylate, 7-[2-(pyrazol-5-yl)-2-methoxycarbonylmethoxyiminoacetamido]-3-(2-acetamidothiazol[5,4-c]pyridinium-5-ylmethyl)-3-cephem-4-carboxylate, 7-[2-(pyrazol-5-yl)-2-ethoxycarbonylmethoxyiminoacetamido]-3-(2-(2-thienyl)oxazolo[5,4-c]pyridinium-5-ylmethyl)-3-cephem-4-carboxylate, 7-[2-(5-aminoisoxazol-3-yl)-2-methoxyiminoacetamido]-3-(2-aminoöxazolo[5,4-b]pyridinium-4-ylmethyl)-3-cephem-4-carboxylate, 7-[2-(2-aminothiazol-4-yl]-2-(2-carboxyprop-2-yl)oxyiminoacetamido]-3-(1H-2-aminoimidazolo[4,5-c]pyridinium-5-ylmethyl)-3-cephem-4-carboxylate, 7-[2-(2-aminothiazol-4-yl)-2-(2-carboxyprop-2-yl)oxyiminoacetamido]-3-(1,2-dimethylimidazolo[4,5-c]pyridinium-5-ylmethyl)-3-cephem-4-carboxylate, 7-[2-(5-amino-1,2,4-oxadiazol-3-yl)-2-(2-carboxyprop-2-yl)oxyiminoacetamido]-3-(1-methyl-2-phenyl-3H-imidazolo[4,5-c]pyridinium-5-ylmethyl)-3-cephem-4-carboxylate, 7-[2-(2-aminothiazol-4-yl)-2-(2-carboxyprop-2-yl)oxyiminoacetamido]-3-(2-formamidothiazolo[5,4-b]pyridinium-4-ylmethyl)-3-cephem-4-carboxylate, 7-[2-(2-aminopyridin-6-yl)-2-methoxyiminoacetamido]-3-(2-aminothiazolo[4,5-c]pyridinium-5-ylmethyl)-3-cephem-4-carboxylate, 7-[2-(2-aminothiazol-4-yl)-2-(2-methoxyiminoacetamido]-3-(2-methoxythiazolo[4,5-c]pyridinium-5-ylmethyl)-3-cephem-4-carboxylate, 7-[2-(2-aminothiazol-4-yl)-2-(2-methoxyiminoacetamido]-3-(2-ethylthiothiazolo[4,5-c]pyridinium-5-ylmethyl)-3-cephem-4-carboxylate, 7-[2-(2-aminothiazol-6-yl)-2-ethoxyiminoacetamido]-3-(2-ethylaminotiazolo[4,5-c]pyridinium-5-yl-methyl)-3-cephem-4-carboxylate, 7-[2-(2-aminopyridin-6-yl)-2-methoxyiminoacetamido[-3-(2-n-butylthiazolo[5,4-c]pyridinium-5-ylmethyl)-3-cephem-4-carboxylate, 7-[2-(2-aminopyridin-6-yl)-2-ethoxycarbonylmethoxyiminoacetamido]-3-(2-aminothiazolo[5,4-b]pyridinium-4-ylmethyl)-3-cephem-4-carboxylate, 7-[2-(5-amino-1,2,4-thiadiazol-3-yl)-2-oximinoacetamido]-3-(2-phenyloxazolo[4,5-b]pyridinium-4-yl-methyl]-3-cephem-4-carboxylate, 7-[2-(2-aminothiazol-4-yl)-2-methoxyiminoacetamido]-3-(2-phenyloxazolo[5,4-c]pyridinium-5-yl-methyl)-3-cephem-4-carboxylate, 7-[2-(2-aminothiazol-4-yl)-2-methoxyiminoacetamido]-3-(2-isopropylthiazolo[5,4-b]pyridinium-4-ylmethyl)-3-cephem-4-carboxylate, 7-[2-(2-aminothiazol-4-yl)-2-methoxyiminoacetamido]-3-(2-ethyl-1-propyl-1H-imidazolo[4,5-b]pyridinium-4-ylmethyl)-3-cephem-4-carboxylate, 7-[2-(2-aminothiazol-4-yl)-2-ethoxyiminoacetamido]-3-(1,2-dimethyl-3H-imidazolo[4,5-c]pyridinium-5-ylmethyl)-3-cephem-4-carboxylate, 7-[2-(pyrazol-5-yl)-2-ethoxycarbonylmethoxyiminoacetamido]-3-(2-(2-thienyl)thiazolo[4,5-b]pyridinium-4-ylmethyl)-3-cephem-4-carboxylate, 7-[2-(2-aminothiazol-4-yl)-2-methoxyiminoacetamido]-3-(2-phenyloxazolo[4,5-b]pyridinium-4-ylmethyl)-3-cephem-4-carboxylate, 7-[2-(2-aminothiazol-4-yl)-2-methoxyiminoacetamido]-3-(2-N,N-diethylaminothiazolo[4,5-c]pyridinium-5-ylmethyl)-3-cephem-4-carboxylate, 7-[2-(5-aminoisoxazol-3-yl)-2-methoxyiminoacetamido]-3-(2-isopropyloxazolo[5,4-c]pyridinium-5-ylmethyl)-3-cephem-4-carboxylate, 7-[2-(2-aminothiazol-4-yl)-2-methoxyiminoacetamido]-3-(2-phenyloxazolo[5,4-b]pyridinium-4-yl-methyl)-3-cephem-4-carboxylate, 7-[2-(2-aminothiazol-4-yl)-2-methoxyiminoacetamido]-3-(2-aminoöxazolo[4,5-c]pyridinium-5-ylmethyl)-3-cephem-4-carboxylate, 7-[2-(2-aminothiazol-4-yl)-2-methoxyiminoacetamido]-3-(2-aminothiazole[4,5-c]pyridinium-5-ylmetyl)-3-cephem-4-carboxylate, 7-[2-(2-aminothiazol-4-yl)-2-(2-carboxyprop-2-yl)oxyiminoacetamido]-3-(2-isobutylthiazolo[5,4-c]pyridinium-5-ylmethyl)-3-cephem-4-carboxylate, 7-[2-(5-amino-1,2,4-thiadiazol-3-yl)-2-methoxyiminoacetamido]-3-(2-butyramido-1H-imidazolo[4,5-c]pyridinium-5-ylmethyl)-3-cephem-4-carboxylate, 7-[2-(pyrazol-5-yl)-2-ethoxycarbonylmethoxyiminoacetamido]-3-[1,2-diethyl-3H-imidazolo[4,5-c]pyridinium-5-ylmethyl)-3-cephem-4-carboxylate, 7-[2-(2-aminothiazol-4-yl)-2-methoxyiminoacetamido]-3-(2-acetamidothiazolo[5,4-b]pyridinium-4-ylmethyl)-3-cephem-4-carboxylate, 7-[2-(2-aminothiazol-4-yl)-2-(2-carboxyprop-2-yl)oxyiminoacetamido]-3-(2-isobutyloxazolo[4,5-b]pyridinium-4-ylmethyl)-3-cephem-4-carboxylate, 7-[2-(2-aminopyrimidin-5-yl)-2-ethoxyiminoacetamido]-3-(2-methyloxazolo[5,4-b]pyridinium-4-yl-methyl)-3-cephem-4-carboxylate, 7-[2-(2-aminothiazol-4-yl)-2-hydroxyiminoacetamido]-3-(thiazolo[5,4-c]pyridinium-5-ylmethyl)-3-cephem-4-carboxylate, 7-[2-(3-aminopyrazol-5-yl)-2-methoxyiminoacetamido]-3-(2-phenylthiazolo[5,4-b]pyridinium-4-ylmethyl)-3-cephem-4-carboxylate, 7-[2-(2-aminothiazol-4-yl)-2-(2-carboxyprop-2-yl)oxyiminoacetamido]-3-(2-(2-thienyl)-3H-imidazolo[4,5-b]pyridinium-4-ylmethyl)-3-cephem-4-carboxylate, and 7-[2-(5-amino-1,2,4-thiadiazol-3-yl)-2-methoxyiminoacetamido]-3-(2-aminoöxazolo[5,4-c]pyridinium-5-ylmethyl)-3-cephem-4-carboxylate.

A preferred group of compounds of the invention is represented by the formula 1 wherein X is N—R[2]. Preferred compounds of the invention are also represented by the formula 1 wherein R is an acyl group and R' is 2-aminothiazol-4-yl and R" is $C_1$-$C_4$ alkyl, preferably methyl, or a carboxy-substituted akyl group, preferably 2-carboxyprop-2-yl, 2-carboxymethyl, or 2-carboxyethyl.

The following detailed examples will further illistrate the invention. Use is made in the examples of the following abbreviations:

TMSI is trimethylsilyliodide; THF is tetrahydrofuran; HPLC is high performance liquid chromatography; NMR is nuclear magnetic resonance spectrum; $DMSOd_6$ is deuterated dimethylsulfoxide; and the letters characterizing the NRM signals are as follows: s is singlet, d is doublet, q is quartet, m is multiplet, t is triplet, v is very, and b is broad. The NMR spectra were run on a JEOL FX-90.

PREPARATION 1

3H-Imidazolo[4,5-c]pyridine was prepared by the method of Stanovik and Tisler, *Synthesis*, 2, 120 (1974). A mixture of 2.2 g (0.02 mole) of 3,4-diaminopyridine and 5 ml of diethoxymethyl acetate was heated at reflux for two hours. The reaction mixture was cooled and diluted by addition of ethyl acetate. The solid precipitate was collected by filtration and sublimed at 170° C. and 50 torr to give 0.84 g of 3H-imidazolo[4,5-c]pyridine; mp 165°-168° C.

Analysis calc. for $C_6H_5N_3$ Theory: C, 60.50; H, 4.23; N, 35.27. Found: C, 60.15; H, 4.32; N, 34.94.

PREPARATIONS 2-4

Following the general procedure of Preparation 1, the following imidazolopyridines were prepared:
1H-imidazolo[4,5-c[pyridine; mp 164°-166° C.
3-methyl-3H-imidazolo[4,5-c]pyridine; mp 82°-88° C.
1-methyl-1H-imidazolo[4,5-c]pyridine; mp 80° C.

PREPARATION 5

A mixture 15.0 g of 3,4-diaminopyridine and 100 ml of acetic anhydride was heated at 120° C. for seventy hours. The reaction mixture was cooled, concentrated and made alkaline to pH 11 by addition of 5N sodium hydroxide. The alkaline solution was extracted with chloroform and the extracts were combined, dried, and concentrated to dryness to give 5.8 g of 1H-2-methyl-imidazolo[4,5-c]pyridine; mp 164°-166° C.

PREPARATIONS 6-7

Similarly prepared were:
1,2-Dimethyl-1H-imidazolo[4,5-c]pyridine; mp 171°-173° C.
2,3-Dimethyl-3H-imidazolo[4,5-c]pyridine; M+ Theory 147; Found 147.

PREPARATION 8-9

A mixture of 1.1 g (10 mM) of 3,4-diaminopyridine, 1.3 g (10 mM) of thiophene-2-carboxylic acid, and 50 g of polyphosphoric acid was heated at 160° C. for four hours. The reaction mixture was added to 100 g of ice and stirred for fifteen minutes. The precipitated solid was collected by filtration and dried to give 500 mg of 2-(2-thienyl)-1H-imidazolo[4,5-c]pyridine; mp 265°-268° C.

Similarly prepared was 2-phenyl-1H-imidazolo[4,5-c]pyridine; 730 mg, single spot tlc (silica, chloroform-methanol; 90:10 v/v).

PREPARATION 10

A mixture of 20 g (0.18 mole) of 2-amino-3-hydroxypyridine in 80 ml of water containing 20 g (0.19 mole) of cyanogen bromide was heated at reflux for fifteen minutes. The reaction mixture was filtered and the filtrate was cooled, neutralized by addition of sodium bicarbonate, and the precipitate that formed was collected by filtration and dried to give, following recrystallization from ethanol and water, 8.66 g of 2-aminooxazolo[4,5-b]pyridine; mp 220°-222° C.

PREPARATION 11

3-Amino-4-hydroxypyridine was reacted with acetic anhydride to afford 4.7 g of 2-methyloxazolo[4,5-c]pyridine; mp 56°-58° C.

PREPARATION 12

Following the procedure of Takahashi, *Chem. Pharm. Bull.* (Tokyo) 2, (1954), 963 mg of 3-nitropyridine-4-thio was reacted with 28.89 g of formic acid and 6.42 g of iron filings to provide, following purification over a silica gel column, 860 mg of thiazolo[4,5-c]pyridine; mp 101°-104° C.

PREPARATION 13

A mixture of 1.3 g of 3-nitropyridine-4-thiol in 4 ml of acetic acid and 15 ml of acetic anhydride containing 1.5 g of zinc dust was heated at reflux for four hours. The reaction mixture was cooled and concentrated to an oil. The oil was dissolved in 5N sodium hydroxide and the alkaline soluton was extracted with diethyl ether. The extracts were combined, dried and concentrated to dryness to afford 557 mg of 2-methylthiazolo[4,5-c]pyridine. M+ Theory 150; Found 150.

PREPARATION 14

3-Nitropyridine-4-thiol was reacted with propionic acid, propionic anhydride and zinc to give 2-ethylthiozolo[4,5-c]pyridine; mp 35° C.

PREPARATION 15

The method described in *J. Het. Chem.*, 14(1), 129(1977) was followed to react 2-chloro-3-aminopyridine with potassium thiocyanate and hydrochloric acid in ethanol to produce 45.3 g of 2-aminothiazolo[5,4-b]pyridine. M+ Theory 151; Found 151.

PREPARATIONS 16-20

The following bicyclic pyridines are prepared by general methods:
2-methylthiazolo[5,4-c]pyridine; mp 93°-95° C.;
2-tert.-butylthiazolo[5,4-c]pyridine; mp 38°-40° C.;
2-N,N-diethylaminothiazolo[5,4-c]pyridine mp 56°-58° C.;
2-ethoxycarbonylthiazolo[5,4-c]pyridine; mp 102°-105° C.;
2-(2-methoxy-4-methylthiophenyl)thiazolo[5,4-c]pyridine; mp 172°-177° C.

EXAMPLE 1 syn-7-[2-(2-Aminothiazol-4-yl)-2-(2-carboxyprop-2-yl)oxyiminoacetamido]-3-(1H-imidazolo[4,5c]pyridinium-5-ylmethyl)-3-cephem-4-carboxylate To a suspension of 1.34 g (2.5 mM) of syn-7-[2-(2-aminothiazol-4-yl)-2-(tert.-butoxycarbonylprop-2-yl)oxyiminoacetamido]-3-acetoxymethyl-3-cephem-4-carboxylic acid in 15 ml of dichloromethane were added in one portion 1.42 ml (8 mM) of N-methyl-N-trimethylsilyltrifluoroacetamide. The reaction mixture was stirred for five minutes at 25° C. under a nitrogen blanket. To the stirred solution were added by pipette 0.88 ml (6.2 mM) of TMSI and the reaction mixture was then stirred at 25° C. for thirty minutes. The solvent was next removed by evaporation under reduced pressure to provide an oil. The oil was dissolved in 6 ml of acetonitrile and 0.84 ml (10.3 mM) of tetrahydrofuran and the solution was stirred for five minutes, whereupon ther was added in one portion a solution of 325 mg (2.7 mM) of 1H-imidazolo[4,5-c]pyridine (from Preparation 2) in 2 ml of acetonitrile containing 1 ml of N-methyl-N-trimethylsilyltrifluoroacetamide. The reaction mixture was stirred for three hours at 25° C. and then added to a mixture of 60 ml of diethyl ether, 35 ml of acetone and 5 ml of methanol. The precipitated solid was collected by filtration to provide 630 mg (b 23% yield) of the product as a solid. The solid was purified by reverse phase $C_{18}$ silica HPLC using acetonitrile-acetic acid-water (10-2-80% by volume) as eluant. Removal of the solvents from the appropriate fractions afforded 120 mg of syn-7-[2-(2-aaminothiazol-4-yl)-2-carboxyprop-2-yl)oxyiminoacetamido]-3-(1H-imidazolo[4,5-c]pyridinium-5-ylmethyl)-3-cephem-4-carboxylate.

IR(KBr): 1776 cm$^{-1}$ β-lactam;
UV (EtOH) $\lambda_{max}$ 220 ε 37,000;
M+ Theory 586; Found 586;
NMR (DMSOd$_6$): signals at 9.75 (s, 1H) δ 9.5 (d, 1H); 8.1 (d, 1H); 8.7 (d, 1H); 7.1 (b s, 2H); 6.7 (s, 1H); 5.7 (m, 1H); 5.15 (d, 1H); 1.4 (s, 6H);

EXAMPLE 2 syn-7-[2-(2-Aminotiazol-4-yl)-2-methoxyiminoacetamido]-3-(1H-imidazolo[4,5-c]pyridinium-5-ylmethyl)-3-cephem-4-carboxylate A suspension of 910 mg (2 mM) of syn-7-[2-(2-aminothiazol-4-yl)-2-methoxyiminoacetamido]-3-acetoxymethyl-3-cephem-4-carboxylic acid in 5 ml of dichloromethane containing 1.24 ml (7 mM) of N-methyl-N-trimethylsilyltrifluoroacetamide was warmed to 40° C. and sonicated for five minutes. The reaction mixture was cooled to 25° C. and stirred while 0.77 ml (5.4 mM) of TMSI were added, and then stirring was continued of 25° C. for thirty minutes. The solvent was next removed by evaporation under reduced pressure and the oil was dissolved in 3 ml of acetonitrile and 0.77 ml (9 mM) of tetrahydrofuran. To this reaction mixture was added a solution of 297 mg (2.5 mM) of 1H-imidazolo[4,5-c]pyridine in 12 ml of acetonitrile containing 1.5 ml of N-methyl-N-trimethylsilyltrifluoroacetamide. The reaction mixture was stirred at 25° C. for three hours and then added to 50 ml of 95% acetone-methanol (v/v). The precipitated solid was collected by filtration (yield 1.09 g) and purified by reverse phase $C_{18}$ silica HPLC using acetonitrileacetic acid-water (4-2-94 percent by volume). There were obtained 390 mg of syn-7-[2-(2-aminothiazol-4-yl)-2-methoxyiminoacetamido]-3-(1H-imidazolo[4,5-c]pyridinium-5-ylmethyl)-3-cephem-4-carboxylate.

IR(KBr): 1772 cm$^{-1}$ β-lactam;
UV (EtOH) $\lambda_{max}$ 212 ε 34,000;
M+ Theory 515; Found 515;
NMR (DMSOd$_6$): signals at δ 9.85 (s, 1H); 9.55 (d, 1H); 8.9 (d, 1H); 8.8 (s, 1H); 8.15 (d, 1H); 7.2 (b s, 2H); 6.7 (s, 1H); 5.7 (m, 1H); 5.15 (d, 1H); 3.8 (s, 3H).

EXAMPLE 3 syn-7-[2-(2-Aminothiazol-4-yl)-2-methoxyiminoacetamido]-3-(3-methyl-3H-imidazolo[4,5-c]pyridinium-5-ylmethyl)-3-cephem-4-carboxylate was prepared according to the procedure of Example 2 by reacting 910 mg (2 mM) of syn-7-[2-(2-aminothiazol-4-yl)-2-methoxyiminoacetamido]-3-acetoxymethyl 4-carboxylic acid with 1.24 ml (7.0 mM) of N-methyl-N-trimethylsilyltrifluoroacetamide and 0.77 ml (5.4 mM) and TMSI to produce the corresponding 3-iodomethyl cephalosporin, and reacting the latter compound in situ with 3-methyl-3H-imidazolo[4,5-c]pyridine. The product was obtained as 920 mg of a white solid. Purification over $C_{18}$ reverse phase HPLC gave 340 mg of title compound.

IR(KBr): 1772 cm$^{-1}$;
UV (EtOH) $\lambda_{max}$ 210 ε 36,500;
M+ Theory 529; Found 529;
NMR (DMSOd$_6$): signals at w 9.5 (d, 1H), 9.4 (d, 1H); 9.05 (s, 1H); 8.35 (d, 1H), 7.2 (b, s, 2H); 6.73 (s, 1H); 5.75 (m, 1H), 5.15 (d, 1H); 4.15 (s, 3H), 3.83 (s, 3H).

EXAMPLES 4–20

The following 3-bicyclicpyridiniummethyl cephalosporins were prepared by the methods of Examples 1–3 by reacting a bicyclic pyridine with a 3-iodomethyl cephalosporin derived from a 3-acetoxymethyl cephalosporin derivative:

syn-7-[2-(2-aminothiazol-4-yl)-2-methoxyiminoacetamido]-3-(1-methyl-1H-imidazolo[4,5-c]pyridinium-5-ylmethyl)-3-cephem-4-carboxylate.
Yield 86%
IR(KBr): 1773 cm$^{-1}$ β-lactam;
UV (EtOH) $\lambda_{max}$ 214 ε 100,000,000;
M+ Theory 529; Found 529.
NMR (DMSOd$_6$): signals at δ 10.1 (s, 1H), 9.45 (d, 1H); 9.1 (d, 1H), 8.8 (s, 1H), 8.3 (d, 1H), 7.15 (b s, 2H), 6.65 (s, 1H), 5.65 (m, 1H), 5.05 (m, 1H), 4.0 (s, 3H), 3.75 (s, 3H).

syn-7-[2-(2-aminothiazol-4-yl)-2-methoxyiminoacetamido]-3-(2-methyl-1H-imidazolo[4,5-c]pyridinium-5-ylmethyl)-3-cephem-4-carboxylate.
Yield 96%. NMR (DMSOd$_6$): signals at δ 9.9 (s, 1H), 9.5 (d, 1H), 8.85 (d, 1H); 8.05 (d, 1H), 7.1 (b s, 2H), 6.66 (s, 1H), 5.7 (m, 1H), 5.1 (d, 1H), 3.75 (s, 3H) 2.7 (s, 3H).

syn-7-[2-(2-aminothiazol-4-yl)-2-methoxyiminoacetamido]-3-(1,2-dimethyl-1H-imidazolo[4,5-c]pyridinium-5-ylmethyl)-3-cephem-4-carboxylate.
Yield 80%
IR(KBr): 1774 cm$^{-1}$ β-lactam; UV (EtOH) $\lambda_{max}$ 218 ε 48,500.
NMR (DMSOd$_6$): signals at δ 9.8 (s, 1H), 9.5 (d, 1H), 9.1 (d, 1H), 8.2 (d, 1H), 7.15 (b s, 2H), 6.65 (s, 1H), 5.6 (m, 1H), 5.05 (m, 1H); 3.9 (s, 3H), 3.75 (s, 3H), 2.7 (s, 3H).

syn-7-[2-(2-aminothiazol-4-yl)-2-methoxyiminoacetamido]-3-(2,3-dimethyl-3H-imidazolo[4,5-c]pyridinium-5-ylmethyl)-3-cephem-4-carboxylate.
Yield 53%

IR(KBr): 1775 cm$^{-1}$ β-lactam;
UV (EtOH) λ$_{max}$ 206 ε 38,000;
M+ Theory 543; Found 543.
NMR (DMSOd$_6$): signals at δ 9.9 (s, 1H), 9.5 (d, 1H), 9.3 (d, 1H), 8.1 (d, 1H), 7.15 (b s, 2H), 6.7 (s, 1H), 5.7 (m, 1H), 5.1 (d, 1H), 3.95 (s, 3H), 3.8 (s, 3H), 2.8 (s, 3H).

syn-7-[2-(2-aminothiazol-4-yl)-2-methoxyiminoacetamido]-3-[2-(2-thienyl)-1H-imidazolo[4,5-c]pyridinium-5-ylmethyl)-3-cephem-4-carboxylate. Yield 18.7%

IR(KBr): 1774 cm$^{-1}$ β-lactam;
UV (EtOH) λ$_{max}$ 247 ε 25,500;
M+ Theory 596; Found 597.
NMR (DMSOd$_6$): signals at δ 9.5 (d, 1H), 9.3 (s, 1H), 8.5 (d, 3H), 7.8 (m, 2H), 7.2 (b s, 2H), 6.7 (s, 1H), 5.7 (m, 1H), 5.1 (d, 1H), 3.8 (s, 3H).

syn-7-[2-(2-aminothiazol-4-yl)-2-methoxyiminoacetamido]-3-(2-phenyl-1H-imidazolo[4,5-c]pyridinium-5-ylmethyl)-3-cephem-4-carboxylate. Yield 620 mg.

IR(KBr): 1772 cm$^{-1}$ β-lactam;
UV (EtOH) λ$_{max}$ 242 ε 39,500;
M+ Theory 591; Found 591.
NMR (DMSOd$_6$): signals at δ 9.5–7.5 (m, 8H), 7.1 (s, 2H), 6.7 (s, 1H), 5.7 (m, 1H), 5.15 (d, 1H), 3. (s, 3H).

syn-7-[2-(2-aminothiazol-4-yl)-2-methoxyiminoacetamido]-3-(2-aminooxazolo[4,5-b]pyridinium-4-ylmethyl)-3-cephem-4-carboxylate. Yield 100%

IR(KBr): 1772 cm$^{-1}$ β-lactam; 1695; 1656;
UV (EtOH) λ$_{max}$ 205, 235, 315 ε 22,746.
NMR (DMSOd$_6$): signals at δ 9.5 (d, 1H), 9.05 (d, 1H), 8.1 (d, 1H), 7.33 (d, 1H), 7.1 (b s, 2H), 6.7 (s, 1H), 5.6 (m, 1H), 5.0 (d, 1H), 3.8 (s, 3H).

syn-7-[2-(2-aminothiazol-4-yl)-2-methoxyiminoacetamido]-3-(2-methyloxazolo[4,5-c]pyridinium-5-ylmethyl)-3-cephem-4-carboxylate. Yield 74%

IR(KBr): 1776 cm$^{-1}$ β-lactam;
UV (EtOH) λ$_{max}$ 203 ε 41,500;
M+ Theory 530; Found 530.
NMR (DMSOd$_6$): signals at δ 10.2 (s, 1H), 9.5 1 (m, 2H), 8.5 (d, 1H), 5.6 (m, 1H), 5.0 (d, 1H), 3.8 (s, 3H), 2.8 (s, 3H).

syn-7-[2-(2-aminothiazol-4-yl)-2-methoxyiminoacetamido]-3-(thiazolo[4,5-c]pyridinium-5-ylmethyl)-3-cephem-4-carboxylate. Yield 95%

IR(KBr): 1773 cm$^{-1}$ β-lactam;
NMR (DMSOd$_6$): signals at δ 10.74 and 9.9 (d, 4H), 7.7 (s, 1H), 6.1 (d, 1H), 3.8 (s, 3H).

syn-7-[2-(2-aminothiazol-4-yl)-2-methoxyiminoacetamido]-3-(2-methylthiazolo[4,5-c]pyridinium-5-yl]-methyl)-3-cephem-4-carboxylate. Yield 48%

IR(KBr): 1777 cm$^{-1}$ β-lactam; 1674; 1623;
UV (EtOH) λ$_{max}$ 227, 260 ε 21,975;
NMR (DMSOd$_6$): signals at δ 10.15 (s, 1H), 9.5 (d, 1H), 9.25 (d, 1H), 8.75 (d, 1H), 5.6 (m, 1H), 5.0 (d, 1H), 3.8 (s, 3H), 2.95 (s, 3H).

syn-7-[2-(2-aminothiazol-4-yl)-2-methoxyiminoacetamido]-3-(2-ethylthiazolo[4,5-c]pyridinium-5-ylmethyl)-3-cephem-4-carboxylate.

IR(KBr): 1772 cm$^{-1}$ β-lactam;
UV (EtOH) λ$_{max}$ 230 ε 46,500;
M+ Theory 559; Found 560.
NMR (DMSOd$_6$): signals at δ 10.15 (s, 1H), 9.35 (d, 1H), 8.8 (d, 1H), 5.6 (m, 1H), 5.0 (d, 1H), 3.8 (s, 3H), 3.3 (q, 2H), 1.4 (t, 3H).

syn-7-[2-(2-aminothiazol-4-yl)-2-methoxyiminoacetamido]-3-(2-aminothiazolo[5,4-b]pyridinium-4-ylmethyl)-3-cephem-4-carboxylate. Yield 100%

UV (EtOH) λ$_{max}$ 250 ε 25,633;
Analysis calculated for C$_{20}$H$_{18}$N$_8$N$_8$O$_5$S$_3$ Theory: C, 43.95; H, 3.32; N, 20.50; S, 17.60. Found: C, 42.07; H, 3.80; N, 17.84; S, 15.71.
NMR (DMSOd$_6$): signals at δ 9.5 (d, 1H), 8.75 (m, 3H), 8.1 (d, 1H), 7.73 (m, 1H), 5.6 (m, 1H), 5.0 (d, 1H), 3.8 (s, 3H).
Titration (66% dimethylformamide in water v/v) pK$_a$ at 4.0, 7.4, 10.7.

syn-7-[2-(2-aminothiazol-4-yl)-2-methoxyiminoacetamido]-3-(2-methylthiazolo[5,4-c]pyridinium-5-ylmethyl)-3-cephem-4-carboxylate. Yield 81%

UV (EtOH) λ$_{max}$ 258 ε 20,563; 223 ε 35,134;
IR (KBr): 1774 cm$^{-1}$ β-lactam; 1666; 1534;
M+ Theory 545; Found 546.
NMR (DMSOd$_6$): δ 9.4 (m, 2H); 8.5 (d, 1H); 7.2 (5, 2H); 6.8 (s, 1H); 5.6 (q, 1H); 5.5 (q, 2H); 5.1 (d, 1H); 3.8 (s, 3H); 3.5 (q, 2H); 3.1 (s, 3H).

syn-7-[2-(2-aminothiazol-4-yl)-2-methoxyiminoacetamido]-3-(2-tert.-butylthiazolo[5,4-c]pyridinium-5-ylmethyl)-3-cephem-4-carboxylate.

UV (EtOH) λ$_{max}$ 222 ε 50,000
IR (KBr) 1777 β-lactam; 1670; 1624; 1534;
M+ Theory 587; Found 588.
NMR (DMSOd$_6$): δ 11.1 (s, 1H); 9.4 (d, 1H); 9.3 (d, 1H); 8.5 (d, 1H); 7.0 (s, 2H); 6.5 (s, 1H); 5.6 (q, 1H); 5.3 (q, 2H); 4.95 (d, 1H); 3.65 (s, 3H); 3.15 (q, 2H); 2.4 (s, 9H).

syn-7-[2-(2-aminothiazol-4-yl)-2-methoxyiminoacetamido]-3-(2-N,N-diethylaminothiazolo[5,4-c]pyridinium-5-ylmethyl)-3-cephem-4-carboxylate.

λmax 228 ε 36,857; 326 ε 28,552;
IR (KBr) 1777 cm$^{-1}$ β-lactam; 1675; 1534;
M+ Theory 603; Found 603.

syn-7-[2-(2-aminothiazol-4-yl)-2-methoxyimino acetamido]-3-(2-ethoxycarbonylthiazolo[4,5-c]pyridinium-5-ylmethyl)-3-cephem-4-carboxylate.

syn-7-[2-(2-aminothiazol-4-yl)-2-methoxyiminoacetamido]-3-[2-(2-methoxy-4-methylthiophenyl)thiazolo[4,5-c]pyridinium-5-ylmethyl]-3-cephem-4-carboxylate.

The 3-bicyclicpyridinium-methyl cephalosporins provided by this invention are useful as antibiotic substances. The compounds have demonstrated excellent antibacterial activity against a wide variety of Gram + and Gram − bacilli. The compounds are particularly effective against diseases caused by Streptococci, *H. influenza, E. coli,* Klebsiella, Enterobacter, Salmonella, and Serratia.

The antibacterial activity of several representative compounds of the invention has been evaluated in standard in vitro agar dilution assays. The following Table presents typical minimum inhibitory concentrations (MIC's) in μg /ml for exemplary compounds when evaluated against typical Gram + and Gram − microorganism. The activity of the known compound ceftazidime is also given by comparison.

TABLE I

| | Agar Dilution MIC (μg/ml) | |
|---|---|---|
| | Cefta- | Compound of Example No. |

TABLE I-continued

| | | Agar Dilution MIC (μg/ml) | | | | | | | | | |
|---|---|---|---|---|---|---|---|---|---|---|---|
| Organism | Strain | zidime | 1 | 2 | 3 | 4 | 5 | 6 | 7 | 8 | 9 |
| Staph. aureus | X1.1 | 8 | 8 | 1 | 1 | 1 | 2 | 2 | 2 | 2 | 2 |
| | V41 | 32 | 32 | 8 | 4 | 8 | 8 | 16 | 16 | 8 | 8 |
| | X400 | 128 | 128 | 64 | 64 | 64 | 32 | 32 | 128 | 32 | 32 |
| | S13E | 32 | 32 | 8 | 4 | 8 | 8 | 8 | 16 | 8 | 8 |
| Staph. epi | EPI1 | 16 | 32 | 4 | 2 | 2 | 4 | 2 | 4 | 4 | 4 |
| | 222 | 16 | 16 | 1 | 1 | 1 | 1 | 1 | 2 | 2 | 2 |
| Strep. A | C203 | 0.125 | 0.06 | <0.008 | <0.008 | 0.15 | <0.008 | <0.008 | 0.015 | <0.008 | <0.008 |
| Strep. PN | PARK | 0.125 | 0.06 | <0.008 | <0.008 | 0.15 | <0.008 | <0.008 | — | <0.008 | <0.008 |
| Strep. D | X66 | >128 | >128 | 128 | >128 | >128 | >128 | >128 | >128 | >128 | >128 |
| | 9960 | 16 | 16 | 2 | 4 | 2 | 8 | 4 | 4 | 4 | 4 |
| H. influ. | C.L. | 0.125 | 0.03 | 0.015 | 0.06 | 0.06 | 0.015 | 0.06 | 0.06 | 0.25 | 0.5 |
| | 76 | 0.125 | 0.06 | 0.015 | 0.06 | 0.06 | 0.015 | — | 0.03 | — | — |
| E. coli | N10 | 0.25 | 0.5 | 0.015 | 0.06 | 0.03 | 0.03 | 0.03 | 0.03 | 1 | 1 |
| | EC14 | 0.125 | 0.125 | <0.008 | <0.008 | <0.008 | <0.008 | <0.008 | 0.015 | 0.25 | 0.125 |
| | TEM | 0.125 | 0.125 | <0.008 | <0.008 | 0.015 | <0.008 | <0.008 | 0.015 | 0.03 | 0.06 |
| Klebsiella | X26 | 0.06 | 0.125 | <0.008 | <0.008 | 0.015 | <0.008 | <0.008 | 0.015 | 0.015 | 0.015 |
| | KAE | 0.5 | 1.0 | 4 | 4 | 4 | 2 | 2 | 2 | 4 | 2 |
| | X68 | 0.125 | 0.125 | <0.008 | 0.03 | 0.015 | 0.015 | 0.03 | 0.03 | 0.5 | 0.5 |
| Enterobacter | | | | | | | | | | | |
| aerogenes | C32 | 0.25 | 1.0 | 0.03 | 0.06 | 0.03 | 0.03 | 0.03 | | 0.5 | 0.5 |
| cloacae | EB5 | 0.125 | 0.25 | 0.06 | 0.06 | 0.03 | 0.06 | 0.03 | | 0.5 | 0.5 |
| Salmonella | X514 | 0.125 | 0.5 | <0.008 | <0.008 | 0.05 | <0.008 | 0.03 | | 0.5 | 0.5 |
| Pseudomonas | X528 | 2 | 8 | 1.0 | 1 | 1 | 2 | 4 | | 64 | 64 |
| | X239 | 2 | 2 | 2 | 2 | 2 | 2 | 4 | | 64 | 64 |
| Serratia | X99 | 0.25 | 0.5 | 0.015 | 0.06 | 0.06 | 0.03 | 0.03 | | 0.5 | 1.0 |

| | | Compound of Example No. | | | | | | | |
|---|---|---|---|---|---|---|---|---|---|
| Organism | Strain | 10 | 11 | 12 | 13 | 14 | 15 | 16 | 17 |
| Staph. aureus | X1.1 | | 0.5 | 1 | 1 | 1 | | 1 | 1 |
| | V41 | 4 | 8 | 2 | 8 | 4 | 2 | 4 | 4 |
| | X400 | 32 | 32 | 2 | 32 | 32 | 32 | 8 | 32 |
| | S13E | 4 | 8 | 8 | 8 | 4 | 4 | 4 | 8 |
| Staph. epi | EPI1 | 2 | 4 | 2 | 2 | 2 | 2 | 2 | 4 |
| | 222 | 1 | 1 | — | 1 | 1 | 16 | 1 | 1 |
| Strep. A | C203 | 0.015 | 0.015 | 0.015 | 0.015 | <0.008 | 0.015 | 0.015 | 0.015 |
| Strep. PN | PARK | 0.015 | 0.015 | 0.015 | <0.008 | <0.008 | — | 0.03 | 0.015 |
| Strep. D | X66 | >128 | >128 | 128 | >128 | >128 | 128 | >128 | >128 |
| | 9960 | 16 | 8 | 4 | 8 | 4 | 8 | 8 | 4 |
| H. influ. | C.L. | 0.06 | 0.125 | 0.06 | 0.03 | 0.06 | 0.06 | 0.06 | 0.25 |
| | 76 | 0.125 | 0.06 | 0.06 | 0.03 | 0.015 | 0.06 | 0.015 | 0.125 |
| E. coli | N10 | 0.125 | 0.06 | 0.03 | 0.03 | 0.03 | 0.03 | 0.06 | 0.5 |
| | EC14 | 0.06 | 0.03 | 0.015 | 0.015 | 0.015 | 0.06 | 0.03 | 0.25 |
| | TEM | 0.03 | 0.03 | 0.03 | 0.015 | 0.015 | 0.03 | 0.03 | 0.06 |
| Klebsiella | X26 | 0.03 | 0.015 | 0.015 | 0.015 | <0.008 | 0.03 | 0.03 | 0.03 |
| | KAE | 4 | 4 | 4 | 2 | 2 | — | 1.0 | 4 |
| | X68 | 0.06 | 0.06 | 0.03 | 0.03 | 0.03 | 4 | 0.06 | 0.5 |
| Enterobacter | | | | | | | | | |
| aerogenes | C32 | 0.125 | 0.06 | 0.03 | 0.03 | 0.06 | 0.03 | 0.06 | 0.5 |
| cloacae | EB5 | 0.25 | 0.125 | 0.06 | 0.06 | 0.06 | 0.06 | 0.125 | 1.0 |
| Salmonella | X514 | 0.06 | 0.03 | 0.03 | 0.06 | 0.06 | 0.03 | 0.03 | 0.5 |
| Pseudomonas | X528 | 4 | 4 | 1 | 2 | 4 | 1 | 8 | 32 |
| | X239 | 2 | 2 | 2 | 8 | 4 | 2 | 4 | 32 |
| Serratia | X99 | 0.125 | 0.125 | 0.06 | 0.06 | 0.06 | 0.06 | 0.125 | 1.0 |

The excellent antibacterial activity of the compounds provided by this invention make them particularly attractive agents for the treatment of a number of diseases of bacterial origin. The treatment of animals suffering from bacterial diseases, or suspected of developing a bacterial infection, is thus another embodiment of this invention. The antibacterial method of treatment provided by this invention will be practiced by administering an antibacterially effective amount of a 3-bicyclic-pyridinium-methyl cephalosporin antibiotic as defined herein to an animal in need of treatment. The method can be practiced therapeutically or prophylactically. The amount of active antibiotic to be administered according to the method will vary depending upon the particular compound selected for use, the severity of the disease being treated or guarded against, the individual undergoing treatment, and related factors commonly encountered with such treatments. Normally, however, the compounds will be administered at a dose of about 0.5 to about 50 mg/kg of animal body weight, and more preferably at a rate of about 1 to about 10 mg/kg. Such amounts will be administered once each day, or more often as needed to treat the particular disease or subject undergoing treatment according to the present method. A typical daily dose for an average adult human will be about 200 to about 500 mg per day.

The antibiotic compounds provided by this invention are especially active when administered by the parenteral route, but they can be formulated for any desired route of administration. Such formulations constitute yet another embodiment of this invention. The formulations of this invention will comprise from about 0.1 to about 95 percent by weight of an active cephalosporin antibiotic of the invention (compounds of formula 1 where R is acyl), admixed with a pharmaceutically acceptable carrier, diluent or excipient therefor. Typical formulations will contain from about 10 to about 60 percent by weight of active ingredient, and more preferably about 20 to about 50 percent.

For convenient oral administration, the compounds can be admixed with any of a number of diluents, excipients and carriers commonly employed in oral formulations, and molded into tablets, pills, troches, or encapsulated into gelatin capsules. Typical carriers, diluents and excipients commonly employed include potato starch, corn starch, sucrose, dextrose, microcrystalline cellulose, dicalcium phosphate, alginic acid, acacia; lubricants such as magnesium stearate; binders such as gum tragacanth or gelatin; and flavoring agents such as peppermint oil, cherry or strawberry flavoring, oil of wintergreen, and the like. The compounds can also be formulated as syrups or elixirs employing common diluents such as a fatty oil, methyl or propyl parabens, suitable dyes and flavoring agents. The compounds can also be formulated in the form of a buccal seal, logenze or other suitable device for sustained controlled delivery of the active ingredient over a prolonged period.

The antibiotics of the invention are preferably formulated for parenteral administration, for example via the intravenous, intramuscular or subcutaneous routes, as well as the transdermal route. Such compositions normally will contain from about 0.1 to about 20.0 percent by weight of active ingredient. Typical excipients, diluents and carriers for parenteral formulations include isotonic saline, dilute aqueous dextrose (eg. 5%), the polyhydric aliphatic alcohols or mixtures thereof, for instance glycerin, propylene glycol, polyethylene glycol, and the like. Parenteral solutions may also contain preservatives such as phenethylalcohol, methyl and propyl parabens, thimerosal and the like. If needed, about 0.05 to about 0.20 percent by weight of an antioxidant such as sodium metabisulfite or sodium bisulfite can also be employed. For intravenous use, preferred formulations will employ an initial concentration down to about 0.05 to about 0.25 mg/ml of active ingredient, and for intramuscular injection, a preferred concentration of active ingredient is about 0.25 to about 0.50 mg/ml.

Examples of typical pharmaceutical formulations provided by this invention include the following.

EXAMPLE 21

Formulation for Intravenous Use

| Ingredient | Amount |
| --- | --- |
| Compound of Example 2 | 1.0 g |
| 0.9% saline | 100 ml |

The intravenous solution can be prepared, for example, with a unit dosage formulation of the antibiotic in a plastic bag or similar container, and by adding the diluent to the container prior to infusion.

EXAMPLE 22

Formulation of Oral Suspension

| Ingredient | Amount |
| --- | --- |
| Compound of Example 8 | 500 mg |
| Sorbitol solution (70% N.F.) | 40 ml |
| Sodium benzoate | 150 mg |
| Saccharin | 10 mg |
| Cherry flavor | 50 mg |

| Ingredient | Amount |
| --- | --- |
| -continued | |
| Distilled water q s ad | 100 ml |

The sorbitol solution is added to 40 ml of distilled water and the cephalosporin is suspended thereon. The saccharin, sodium benzoate, and flavoring are added and dissolved. The volume is adjusted to 100 ml with distilled water. Each ml of syrup contains 5 mg of the cephalosporin antibiotic. This oral formulation is ideally suited for pediatric use.

EXAMPLE 23

Preparation of 250 mg capsule

| Ingredient | Amount |
| --- | --- |
| Compound of Example 10 | 250 mg |
| Lactose | 150 mg |
| Corn starch | 100 mg |
| | 500 mg |

The ingredients are blended to uniformity and encapsulated into gelatin capsules. Such capsules are orally administered at the rate of about one each day for the treatment of upper respiratory bacterial infections, including pharyngitis and tonsillitis.

EXAMPLE 24

Preparation of Parenteral Solution

In a solution of 700 ml of propylene glycol and 200 ml of distilled water for injection is dissolved 20.0 grams of the compound of Example 13, as the hydrochloride salt. The pH of the solution is adjusted to 5.5 with hydrochloric acid, and the volume is made up to 1000 ml with distilled water. The formulation is sterilized, filled into 5.0 ml ampoules each containing 2.0 ml (representing 40 mg of active ingredient) and sealed under nitrogen.

The compounds of the invention additionally may be administered intrarectally for examle in a suitably formulated suppository. Pharmaceutically acceptable suppository formulations can be prepared with the antibiotic compound and a suppository composition such as cocoa butter, hydrogenated fats, glycerides, or polyethylene glycols.

Pharmaceutical compositions of the invention also include unit dosage formulations. Such formulations comprise between about 200 mg. and about 10 g. of the antibiotic or a pharmaceutically acceptable nontoxic salt thereof in solid form in a sterile ampoule, vial or a plastic container such as a bag adapted for i.v. administration. The antibiotic may be amorphous or in the crystalline state. Such formulations may also contain a buffering agent, solubilizing agent, clarifying agent, stabilizing agent, or other excipient. An example of a pharmaceutical composition of this invention for i.v. use comprises 500 mg. of the dry powder of the antibiotic or a pharmaceutically acceptable salt thereof in a 10 ml. sterile rubber-stoppered ampoule. Another such composition comprises 4 g. of dry powder of the antibiotic in a 100 ml. sterile ampoule. A further composition comprises 10 g. of the antibiotic as a dry powder in a sealed, sterile plastic pouch.

I claim:

1. A compound of the formula

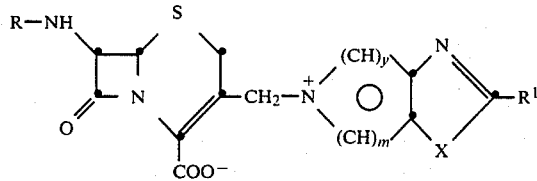

wherein R is hydrogen, formyl, α-aminodipoyl, protected α-aminoadipoyl, or an acyl group of the formula

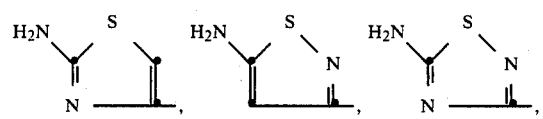

wherein
R' is 5- or 6-membered heterocyclic ring of the formulas

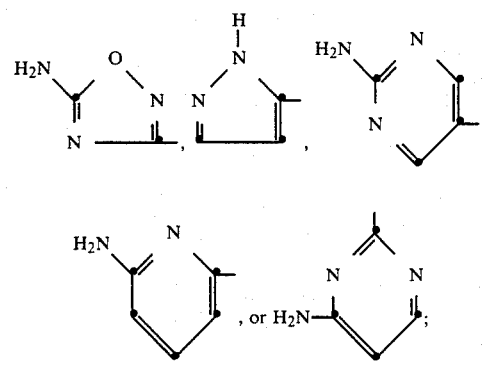

R" is hydrogen, $C_1$–$C_4$ alkyl, a carboxy-substituted alkyl or carboxy-substituted cycloalkyl group of the formula

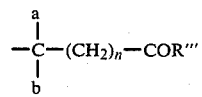

wherein n is 0–3; a and b when taken separately are independently hydrogen or $C_1$–$C_3$ alkyl, and when taken together with the carbon to which they are bonded form a $C_3$–$C_7$ carbocyclic ring; R''' is hydroxy, $C_1$–$C_4$ alkoxy, amino, or OR°, wherein R° is indanyl, phthalidyl, or an acyloxymethyl group of the formula —$CH_2$—O—C(O)—$R_2$ wherein $R_2$ is $C_1$–$C_4$ alkyl or phenyl; or R° is a carboxy-protecting group;

or R" is an N-substituted carbamoyl group of the formula

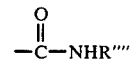

wherein
R"" is $C_1$–$C_4$ alkyl, phenyl or $C_1$–$C_3$ alkyl substituted by phenyl;

y and m independently are integers equal to 0, 1, 2 or 3, provided that y plus m equals 3;

$R^1$ is hydrogen, $C_1$–$C_4$ alkyl, $C_1$–$C_4$ alkoxy, $C_1$–$C_4$ alkylthio, thienyl, amino, $C_1$–$C_4$ alkanoylamino, $C_1$–$C_4$ alkylamino, di-$C_1$–$C_4$ alkylamino, hydroxycarbonyl, $C_1$–$C_4$ alkoxycarbonyl, or phenyl or phenylcarbonyl in which the phenyl groups may be subsituted by one or two groups selected from $C_1$–$C_4$ alkoxy, $C_1$–$C_4$ alkyl or $C_1$–$C_4$ alkylthio;

X is O or S; and the pharmaceutically acceptable salts and biologically labile esters thereof.

2. The compound of claim 1 wherein R is an acyl group of the formula

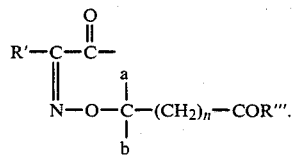

3. The compound of claim 2 wherein R is

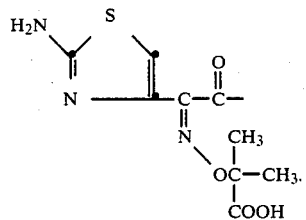

4. The compound of claim 1 wherein R is an acyl group of the formula

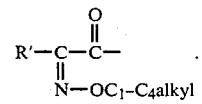

5. The compound of claim 4 wherein R is an acyl group of the formula

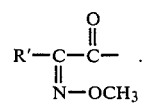

6. The coupound of claim 5 wherein R' is

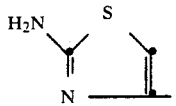

7. The compound of claim 6 wherein X is 0.
8. The compound of claim 1 wherein $R^1$ is hydrogen.
9. The compound of claim 1 wherein $R^1$ is $C_1$-$C_4$ alkyl.
10. The compound of claim 1 wherein $R^1$ is phenyl.
11. The compound of claim 1 wherein $R^1$ is thienyl.
12. The compound of claim 1 wherein $R^1$ is amino.

13. A compound of claim 1 having the formula

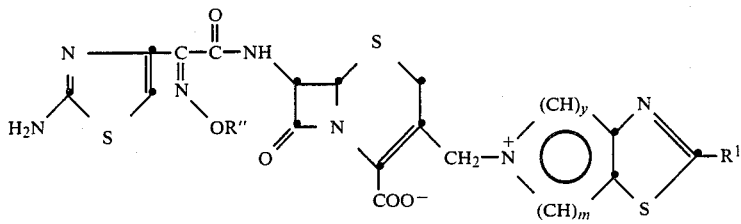

wherein:
R" is hydrogen $C_1$-$C_4$ alkyl, a carboxy-substituted alkyl or carboxy-substituted cycloalkyl roup of the formula

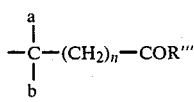

wherein n is 0-3; a and b when taken separately are independently hydrogen or $C_1$-$C_3$ alkyl, and when taken together with the carbon to which they are bonded form a $C_3$-$C_7$ carbocyclic ring; R''' is hydroxy, $C_1$-$C_4$ alkoxy, amino, or OR°, wherein R° is indanyl, phthalidyl, or an acyloxymethyl group of the formula —$CH_2$—O—C(O)—$R^2$ wherein $R^2$ is $C_1$-$C_4$ alkyl or phenyl; or R° is a carboxy-protecting group;
or R" is an N-substituted carbamoyl group of the formula

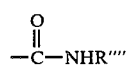

wherein R'''' is $C_1$-$C_4$ alkyl, phenyl or $C_1$-$C_3$ alkyl substituted by phenyl;

y and m independently are intergers equal to 0, 1, 2 or 3, provided that y plus m equals 3;
$R^1$ is hydrogen, $C_1$-$C_4$ alkyl, $C_1$-$C_4$ alkoxy, $C_1$-$C_4$ alkylthio, thienyl, amino, $C_1$-$C_4$ alkanoylamino; $C_1$-$C_4$ alkylamino, di-$C_1$-$C_4$ alkylamino, hydroxycarbonyl, $C_1$-$C_4$ alkoxycarbonyl, or phenyl or phenylcarbonyl in which the phenyl groups may be substituted by one or two groups selected from $C_1$-$C_4$ alkoxy, $C_1$-$C_4$ alkyl or $C_1$-$C_4$ alkylthio;
and the pharmaceutically acceptable salts and biologically labile esters thereof.

14. The compound of claim 13 wherein R" is hydrogen, $C_1$-$C_4$ alkyl or 2-carboxyprop-2-yl.

15. The compound of claim 14 having the formula

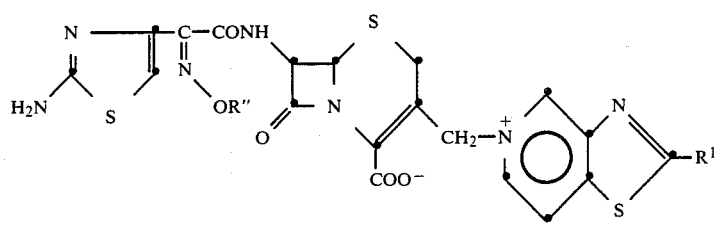

wherein R" is methyl, ethyl or 2-carboxyprop-2-yl and $R^1$ is hydrogen, amino, methyl or methylthio.

16. The compound of claim 15, said compound being syn-7-[2-(2-aminothiazol-4-yl)-2-methoxyiminoacetamido]-3-(thiazolo[4,5-c]pyridinium-5-ylmethyl)-3-cephem-4-carboxylate.

17. The compound of claim 15, said compound being syn-7-[2-(2-aminothiazol-4-yl)-2-methoxyiminoacetamido]-3-(2-methylthiazolo[4,5-c]pyridinium-5-ylmethyl)-3-cephem-4-carboxylate.

18. The compound of claim 15, said compound being syn-7-[2-(2-aminothiazol-4-yl)-2-ethoxyiminoacetamido]-3-(thiazolo[4,5-c]pyridinium-5-ylmethyl)-3-cephem-4-carboxylate.

19. The compound of claim 15, said compound being syn-7-[2-(2-aminothiazol-4-yl)-2-(2-carboxyprop-2-yl)oxyiminoacetamido]-3-(thiazolo[4,5-c]pyridinium-5-ylmethyl)-3-cephem-4-carboxylate.

20. The compound of claim 15, said compound being syn-7-[2-(2-aminothiazol-4-yl)-2-ethoxyiminoacetamido]-3-(2-aminothiazolo[4,5-c]pyridinium-5-ylmethyl)-3-cephem-4-carboxylate.

21. The compound of claim 15, said compound being syn-7-[2-(2-aminothiazol-4-yl)-2-(2-carboxyprop-2-yl)oxyiminoacetamido]-3-(2-aminothiazolo[4,5-c]pyridinium-5-ylmethyl)-3-cephem-4-carboxylate.

22. syn-7-[2-(2-aminothiazol-4-yl)-2-methoxyiminoacetamido]-3-(2-methylthiothiazolo[4,5-c]pyridinium-5-ylmethyl)-3-cephem-4-carboxylate.

23. The compound of claim 14 having the formula

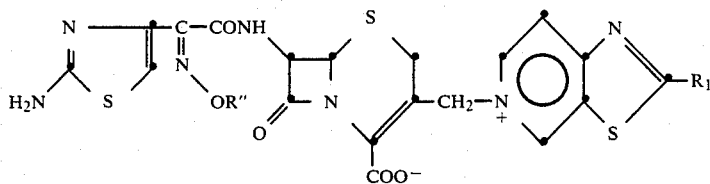

wherein R" is methyl, ethyl or 2-carboxyprop-2-yl and R¹ is hydrogen, amino, methyl or methylthio.

24. The compound of claim 23, said compound being syn-7-[2-(2-aminothiazol-4-yl)-2-methoxyiminoacetamido]-3-(2-methylthiazolo[5,4-c]pyridinium-5-ylmethyl)-3-cephem-4-carboxylate.

25. A pharmaceutical formulation comprising a compound of claim 1 admixed with a pharmaceutically acceptable carrier, excipient or diluent therefor.

26. The formulation of claim 25 employing a compound wherein R is an acyl group of the formula

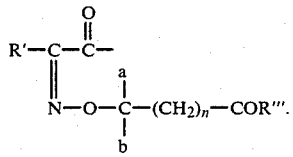

27. The formulation of claim 26 employing a compound wherein R is

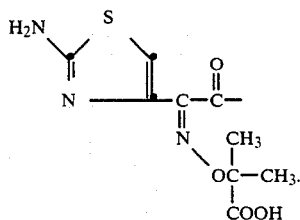

28. The formulation of claim 27 employing syn-7-[2-(2-aminothiazol-4-yl)-2-(carboxyprop-2-yl)oxyiminoacetamido]-3-(thiazolo[4,5-c]pyridinium-5-ylmethyl)-3-cephem-4-carboxylate.

29. The formulation of claim 25 employing a compound wherein R is

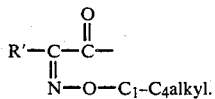

30. The formulation of claim 29 employing a compound of the formula

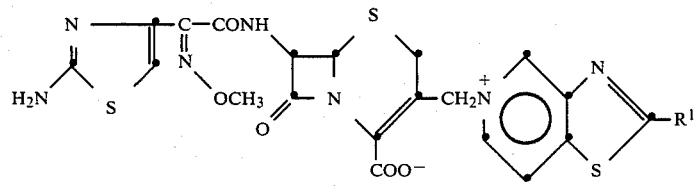

wherein R¹ is hydrogen, amino, methyl or methylthio.

31. The formulation of claim 30 employing syn-7-[2-(2-aminothiazol-4-yl)-2-methoxyiminoacetamido]-3-(2-methylthiazolo[4,5-c]pyridinium-5-ylmethyl)-3-cephem-4-carboxylate.

32. The formulation of claim 29 wherein R is

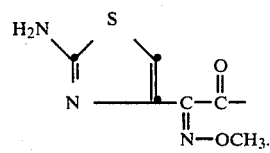

33. The formulation of claim 32 employing a compound wherein X is 0.

34. The formulation of claim 32 employing a compound wherein X is S, y is 2 and m is 1.

35. A method for treating bacterial infections in animals which comprises administering to an animal an antibacterial amount of a compound of claim 1.

36. The method of claim 35 employing a compound wherein R is an acyl group of the formula

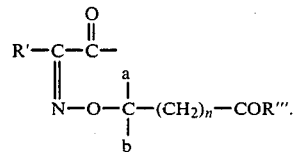

37. The method of claim 36 a compound wherein R is

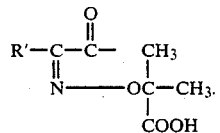

38. The method of claim 37 employing a compound wherein R is

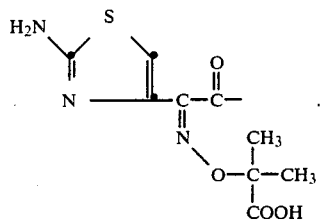

39. The mehod of claim 38 employing a compound wherein X is S.

40. The method of claim 39 employing a compound wherein $R^1$ is hydrogen, amino, methyl or methylthio.

41. The method of claim 35 employing a compound wherein R is an acyl group of the formula

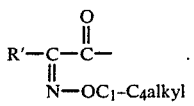

42. The method of claim 41 employing a compound wherein R is

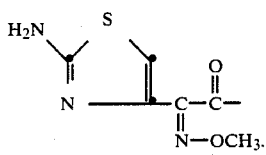

43. The method of claim 42 employing a compound wherein X is 0.

44. The method of claim 42 employing a compound wherein X is S, y is 2 and m is 1.

45. The method of claim 42 employing a compound of the formula

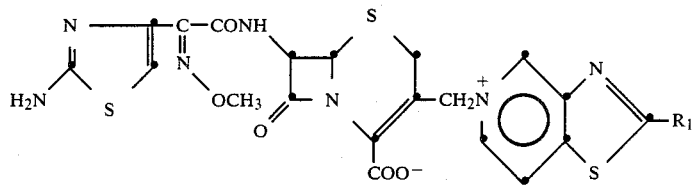

wherein $R^1$ is hydrogen, methyl, amino, or methylthio.

46. The method of claim 45 employing syn-7-[2-(2-aminothiazol-4-yl)-2-methoxyiminoacetamido]-3-(2-methylthiazolo[4,5-c]pyridinium-5-ylmethyl)-3-cephem-4-carboxyate.

47. A compound of the formula

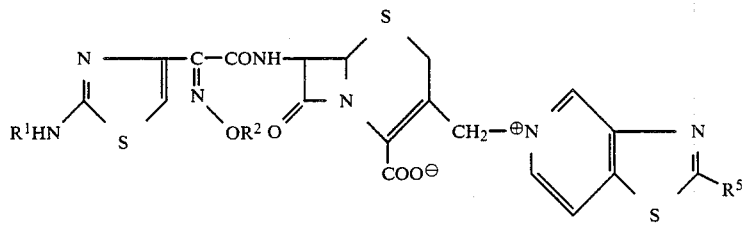

wherein $R^1$ is hydrogen or a conventional amino-protecting group, $R^2$ is a straight or branched chain alkyl group containing from 1 to 4 carbon atoms or a group of the formula

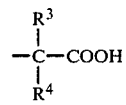

in which $R^3$ and $R^4$ each are independently hydrogen, methyl or ethyl, or $R^3$ and $R^4$, taken together with the carbon atom to which they are attached, may be a cycloalkylidene ring containing from 3 to 5 carbon atoms, and $R^5$ is hydrogen, carboxy, amino, (lower)alkylamino, di(lower)alkylamino, (lower)alkyl, (lower) alkoxy, (lower) alkylthio, or $R^5$ is a group of the formula

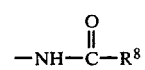

in which $R^8$ is hydrogen or (lower)alkyl, or a nontoxic pharmaceutically acceptable salt or physiologically hydrolyzable ester thereof.

48. A compound of claim 47 wherein $R^1$ is hydrogen and $R^2$ is methyl, ethyl, carboxymethyl, or a group of the formula

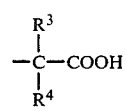

in which $R^3$ and $R^4$ each of methyl, or $R^3$ and $R^4$, taken together with the carbon atom to which they are attached, are cyclopropylidene or cyclobutylidene, or a nontoxic pharmaceutically acceptable salt or physiologically hydrolyzable ester thereof.

49. A compound of claim 1 wherein $R^1$ is hydrogen, $R^2$ is methyl, ethyl, 2-carboxyprop-2-yl, carboxymethyl or 1-carboxycyclobut-1-yl, and $R^5$ is hydrogen methyl, (lower)alkanoylamino, di(lower)alkylamino, formylamino, or amino, or a non-toxic pharmaceutically acceptable salt or physiologically hydrolyzable ester thereof.

50. The compound of claim 47 which is 7-[(Z)-2-(2-aminothiazol-4-yl)-2-methoxyiminoacetamido]-3-{(5-thiazolo[4,5-c]-pyridino)methyl}-3-cephem-4-carboxylate, or a nontoxic pharmaceutically acceptable salt or physiologically hydrolyzable ester thereof.

51. The compound of claim 47 which is 7-[(Z)-2-(2-aminothiazol-4-yl)-2-(2-carboxyprop-2-oxyimino)acetamido]-3-{(5-thiazolo[4,5-c]pyridino)methyl}-3-cephem-4-carboxylate, or a nontoxic pharmaceutically acceptable salt or physiologically hydrolyzable ester thereof.

52. The compound of claim 47 which is 7-[(Z)-2-(2-aminothiazol-4-yl)-2-ethoxyiminoacetamido]-3-{(5-thiazolo[4,5-c]-pyridino)methyl}-3-cephem-4-carboxylate, or a nontoxic pharmaceutically acceptable salt or physiologically hydrolyzable ester thereof.

53. The compound of claim 47 which is 7-[(Z)-2-(2-aminothiazol-4-yl)-2-methoxyiminoacetamido]-3-[{5-(2-aminothiazolo[4,5-c]pyridino)}methyl]-3-cephem-4-carboxylate, or a nontoxic pharmaceutically acceptable salt or physiologically hydrolyzable ester thereof.

54. The compound of claim 47 which is 7-[(Z)-2-(2-aminothiazol-4-yl)-2-methoxyiminoacetamido]-3-[{5-(2-methylthiazolo[4,5-c]pyridino)}methyl]-3-cephem-4-carboxylate, or a nontoxic pharmaceutically acceptable salt or physiologically hydrolyzable ester thereof.

55. The compound of claim 47 which is 7-[(Z)-2-(2-aminothiazol-4-yl)-2-(2-carboxyprop-2-oxyimino)acetamido]-3-]{5-(2-aminothiazolo[4,5-c]pyridino)}methyl]-3-cephem-4-carboxylate, or a nontoxic pharmaceutically acceptable salt or physiologically hydrolyzable ester thereof.

56. The compound of claim 47 which is 7-[(Z)-2-(2-aminothiazol-4-yl)-2-methoxyiminoacetamido]-3-(2-dimethylamino-5-thiazolo[4,5-c]pyridino)methyl-3-cephem-4-carboxylate, or a nontoxic pharmaceutically acceptable salt or physiologically hydrolyzable ester thereof.

57. A method of combatting bacterial infection in a warm-blooded animal in need of such treatment comprising administering to said warm-blooded mammal an antibacterially effective amount of at least one compound of claim 47.

58. An antibacterial composition comprising an antibacterially effective amount of at least one compound of claim 47 and an inert pharmaceutical carrier.

59. An antibacterial composition in unit dosage form comprising from about 50 mg to about 1500 mg of at least one compound of claim 47 and an inert pharmaceutical carrier.

* * * * *